US008299214B2

(12) United States Patent
Sato et al.

(10) Patent No.: US 8,299,214 B2

(45) Date of Patent: Oct. 30, 2012

(54) INFLUENZA INFECTION-INHIBITING PEPTIDE, INFLUENZA VIRUS INFECTION INHIBITOR, LIPOSOME, AND INFLUENZA PREVENTIVE/THERAPEUTIC AGENT

(75) Inventors: Toshinori Sato, Kanagawa (JP); Teruhiko Matsubara, Kanagawa (JP)

(73) Assignee: Keio University, Tokyo (JP)

( * ) Notice: Subject to any disclaimer, the term of this patent is extended or adjusted under 35 U.S.C. 154(b) by 706 days.

(21) Appl. No.: 12/282,807

(22) PCT Filed: Mar. 7, 2007

(86) PCT No.: PCT/JP2007/054452

§ 371 (c)(1), (2), (4) Date: Aug. 11, 2009

(87) PCT Pub. No.: WO2007/105565

PCT Pub. Date: Sep. 20, 2007

(65) Prior Publication Data

US 2010/0119588 A1 May 13, 2010

(30) Foreign Application Priority Data

Mar. 13, 2006 (JP) ................................ 2006-068020

(51) Int. Cl.
*C07K 7/06* (2006.01)

(52) U.S. Cl. ......... 530/328; 530/327; 530/329; 530/330

(58) Field of Classification Search ........... 530/327–331
See application file for complete search history.

(56) References Cited

U.S. PATENT DOCUMENTS

| | | | | |
|---|---|---|---|---|
| 5,104,854 | A * | 4/1992 | Schlesinger et al. | 514/3.7 |
| 5,298,490 | A * | 3/1994 | Heavner et al. | 514/3.7 |
| 6,150,131 | A * | 11/2000 | Palese | 435/69.1 |
| 6,337,070 | B1 * | 1/2002 | Okuno et al. | 424/186.1 |
| 2004/0171536 | A1 * | 9/2004 | Lipps et al. | 514/12 |
| 2005/0202415 | A1 * | 9/2005 | Bogoch et al. | 435/5 |

FOREIGN PATENT DOCUMENTS

| | | | |
|---|---|---|---|
| EP | 1167382 | * | 1/2002 |
| EP | 1167382 | A1 | 1/2002 |
| JP | 1991-103180 | A | 4/1991 |
| JP | 2002-284798 | | 10/2002 |
| JP | 2006-101709 | | 4/2006 |
| WO | WO 00/59932 | | 10/2000 |
| WO | WO2006/114478 | | 11/2006 |

OTHER PUBLICATIONS

Lobo et al., "Active Site Studies of Human Thrombin and Bovine Trypsin: Peptide Substrates," *Arch. Biochem. Biophys.* 177:235-244 (1976.)

Sato et al., "Inhibition of Influenza Virus Infection by Hemagglutinin-Binding Peptides," *Pept. Sci.* 38:329-330 (2002) (volume date 2001).

Sequence No. 148 in the sequence listing of Japanese Patent Application JP 2003-523189, p. 112, filed Aug. 5, 2003.

Sequence Nos. 9553-9556 in the sequence listing of International Patent Application Publication No. WO 2003/106491, filed Feb. 5, 2004.

Table 4b No. 43 of JP 2005-533855, pp. 51-52, filed Nov. 10, 2005.

Conference of the chemical society of Japan (CSJ) abstract vol. 85 No. 2 p. 1223 (2005).

English translation of Conference of the chemical society of Japan (CSJ) abstract vol. 85 No. 2 p. 1223 (2005).

* cited by examiner

*Primary Examiner* — David Lukton

(74) *Attorney, Agent, or Firm* — Clark & Elbing LLP

(57) ABSTRACT

To provide peptides having high affinity for hemagglutinin and peptides having high inhibitory activity against influenza virus infection, as well as pharmaceutical compositions containing the peptides, the polypeptides having any one of SEQ ID NOs: 2 to 7, 9 to 10, and 12 to 18 are obtained by introducing mutation into a peptide having the sequence of ARLSPTMVHPNGAQP (peptide A-1: SEQ ID NO: 1) and screening for peptides having higher affinity for hemagglutinin. Further, the inhibitory activity of the peptide of SEQ ID NO: 3 against influenza virus infection can be enhanced by truncating SEQ ID NO: 3 in its C-terminus region with leaving ARLPR (SEQ ID NO: 44) or ARLP (SEQ ID NO: 52). In addition, an influenza virus-infection inhibitor and an influenza preventive/therapeutic agent can be prepared by formulating these influenza virus receptor-binding peptides.

10 Claims, 4 Drawing Sheets

SEQUENCE LISTING

```
<160> NUMBER OF SEQ ID NOS: 62

<210> SEQ ID NO 1
<211> LENGTH: 15
<212> TYPE: PRT
<213> ORGANISM: Artificial Sequence
<220> FEATURE:
<223> OTHER INFORMATION: Hemagglutinin-binding peptide (A-1)

<400> SEQUENCE: 1

Ala Arg Leu Ser Pro Thr Met Val His Pro Asn Gly Ala Gln Pro
1               5                   10                  15


<210> SEQ ID NO 2
<211> LENGTH: 15
```

<212> TYPE: PRT
<213> ORGANISM: Artificial Sequence
<220> FEATURE:
<223> OTHER INFORMATION: Hemagglutinin-binding peptide

<400> SEQUENCE: 2

Ala Arg Leu Ser Pro Asn Met Val His Leu Asn Pro Ala Gln Pro
1 5 10 15

<210> SEQ ID NO 3
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 3

Ala Arg Leu Pro Arg Thr Met Val His Pro Lys Pro Ala Gln Pro
1 5 10 15

<210> SEQ ID NO 4
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 4

Ala Arg Leu Ser Pro Thr Met Val His Pro His Pro Ala Lys Ser
1 5 10 15

<210> SEQ ID NO 5
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 5

Ala Arg Leu Pro Pro Thr Met Val Arg Pro Asn Gly Pro Gln Pro
1 5 10 15

<210> SEQ ID NO 6
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 6

Ala Arg Leu Pro Pro Ala Met Val Arg Pro Asn Gly Pro Gln Pro
1 5 10 15

<210> SEQ ID NO 7
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 7

Ala Arg Leu Ser Pro Thr Met Val Arg Pro Ile Gly Ala Gln Pro
1 5 10 15

<210> SEQ ID NO 8
<211> LENGTH: 15
<212> TYPE: PRT
<213> ORGANISM: Artificial Sequence -continued
<220> FEATURE:
<223> OTHER INFORMATION: Hemagglutinin-binding peptide

<400> SEQUENCE: 8

Ala Arg Leu Ser Pro Thr Met Val His Leu Asn Gly Ala Gln Pro
1 5 10 15

<210> SEQ ID NO 9
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 9

Thr Arg Leu Ser His Ile Met Val His Arg Asn Gly Ala Gln Pro
1 5 10 15

<210> SEQ ID NO 10
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 10

Thr Arg Leu Pro Pro Ala Met Val His Pro Asn Gly Ala Gln His
1 5 10 15

<210> SEQ ID NO 11
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 11

Ala Arg Leu Ser Pro Thr Met Val His Pro Asn Gly Ala Gln His
1 5 10 15

<210> SEQ ID NO 12
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 12

Ala Arg Leu Ser Pro Ala Met Val His Pro Asn Gly Ala Arg Leu
1 5 10 15

<210> SEQ ID NO 13
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 13

Ala Arg Leu Ser Pro Ala Met Val Arg Pro Asn Gly Ala Arg Pro
1 5 10 15

<210> SEQ ID NO 14
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 14

Ala Arg Leu Ser Pro Thr Met Val His Arg His Gly Ala Gln Pro
1 5 10 15

<210> SEQ ID NO 15
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 15

Thr Arg Leu Pro Pro Thr Met Ile His Pro Asn Gly Ala Gln Pro
1 5 10 15

<210> SEQ ID NO 16
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 16

Ala Arg Leu Ser Pro Thr Met Val His Pro Arg Gly Ala Gln Pro
1 5 10 15

<210> SEQ ID NO 17
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 17

Ala Arg Leu Ser Pro Thr Met Val His Arg Asn Gly Val Gln Pro
1 5 10 15

<210> SEQ ID NO 18
<211> LENGTH: 15
<212> TYPE: PRT
<213> ORGANISM: Artificial Sequence
<220> FEATURE:
<223> OTHER INFORMATION: Hemagglutinin-binding peptide

<400> SEQUENCE: 18

Thr Arg Leu Pro Pro Ala Met Ala Arg Pro Asn Ser Ala Gln Pro
1 5 10 15

<210> SEQ ID NO 19
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 19
gcgcgtttgt ctcctactat ggttcatcct aatggtgcgc agcct 45

<210> SEQ ID NO 20
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 20

```
gcgcgtttgt cgcctaatat ggttcatctt aatcctgcgc agcct                45


<210> SEQ ID NO 21
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 21

gcgcgtttgc ctcgtactat ggttcatcct aaacctgcgc agcca                45


<210> SEQ ID NO 22
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 22

gcgcgactgt ctcctactat ggttcatcct catcccgcga agtct                45


<210> SEQ ID NO 23
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 23

gcgcgtttgc ctcctactat ggttcgtcct aatggtccgc agcct                45


<210> SEQ ID NO 24
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 24

gcgcgtttgc ctcctgctat ggttcgtcct aatggtccgc agcct                45


<210> SEQ ID NO 25
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 25

gcacgtttgt cacctactat ggttcgtcct attggtgcac agcct                45


<210> SEQ ID NO 26
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 26

gcgcgtttgt ctcctactat ggttcatctt aatggtgcgc agcct                45


<210> SEQ ID NO 27
<211> LENGTH: 45
<212> TYPE: DNA
<213> ORGANISM: Artificial Sequence
<220> FEATURE:
```

<223> OTHER INFORMATION: Sequence encoding hemagglutinin-binding peptide

<400> SEQUENCE: 27
acgcgtttgt ctcatattat ggttcatcgt aatggtgcgc agcct 45

<210> SEQ ID NO 28
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 28
acgcgtttgc ctcctgctat ggtccatcct aatggagccc agcat 45

<210> SEQ ID NO 29
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 29
gcgcgtttgt ctcctactat ggtccatcct aatggtgcgc agcat 45

<210> SEQ ID NO 30
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 30
gcgcgtttgt ctcccgctat ggtacatcct aatggtgcgc ggctt 45

<210> SEQ ID NO 31
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 31
gcgcgtttgt ctcctgctat ggttcgtcct aatggtgcgc ggcct 45

<210> SEQ ID NO 32
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 32
gcgcgtttgt ctccaactat ggttcatcgt catggtgcgc agcct 45

<210> SEQ ID NO 33
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 33
actcgtttgc ctcctactat gattcatcct aatggtgcgc agcct 45

<210> SEQ ID NO 34

<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 34
gcgcgtttgt ctcctactat ggttcatcct agaggtgctc agcct 45

<210> SEQ ID NO 35
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 35
gcgcgtttgt ctcctactat ggttcatcgt aatggtgtgc agcct 45

<210> SEQ ID NO 36
<211> LENGTH: 45
<212> TYPE: DNA
<213> ORGANISM: Artificial Sequence
<220> FEATURE:
<223> OTHER INFORMATION: Sequence encoding hemagglutinin-binding peptide

<400> SEQUENCE: 36
acgcgtttgc ctccagctat ggctcgtcct aatagcgcac agcct 45

<210> SEQ ID NO 37
<211> LENGTH: 15
<212> TYPE: PRT
<213> ORGANISM: Artificial Sequence
<220> FEATURE:
<223> OTHER INFORMATION: Consensus sequence for hemagglutinin-binding peptides
<220> FEATURE:
<221> NAME/KEY: MISC_FEATURE
<222> LOCATION: (1)..(1)
<223> OTHER INFORMATION: Xaa = Ala, Arg, Asn, Asp, Cys, Gln, Glu, Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (4)..(4)
<223> OTHER INFORMATION: Xaa = Ser or Pro
<220> FEATURE:
<221> NAME/KEY: MISC_FEATURE
<222> LOCATION: (5)..(5)
<223> OTHER INFORMATION: Xaa = Ala, Arg, Asn, Asp, Cys, Gln, Glu, Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (6)..(6)
<223> OTHER INFORMATION: Xaa = Ala, Arg, Asn, Asp, Cys, Gln, Glu, Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (9)..(9)
<223> OTHER INFORMATION: Xaa = His or Arg
<220> FEATURE:
<221> NAME/KEY: MISC_FEATURE
<222> LOCATION: (10)..(10)
<223> OTHER INFORMATION: Xaa = Ala, Arg, Asn, Asp, Cys, Gln, Glu, Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (11)..(11)
<223> OTHER INFORMATION: Xaa = Ala, Arg, Asn, Asp, Cys, Gln, Glu, Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (12)..(12)
<223> OTHER INFORMATION: Xaa = Ala, Arg, Asn, Asp, Cys, Gln, Glu, Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (13)..(13)
<223> OTHER INFORMATION: Xaa = Ala, Arg, Asn, Asp, Cys, Gln, Glu, Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (15)..(15)
<223> OTHER INFORMATION: Xaa = Ala, Arg, Asn, Asp, Cys, Gln, Glu, Gly, His, Ile, Leu, Lys, Met, Phe, Pro, Ser, Thr, Trp, Tyr, or Val

<400> SEQUENCE: 37

```
Xaa Arg Leu Xaa Xaa Xaa Met Val Xaa Xaa Xaa Xaa Xaa Gln Xaa
1               5                   10                  15
```

<210> SEQ ID NO 38
<211> LENGTH: 8
<212> TYPE: PRT
<213> ORGANISM: Artificial Sequence
<220> FEATURE:
<223> OTHER INFORMATION: Influenza virus infection-inhibiting peptide s2 (1-8)

<400> SEQUENCE: 38

```
Ala Arg Leu Pro Arg Thr Met Val
1               5
```

<210> SEQ ID NO 39
<211> LENGTH: 7
<212> TYPE: PRT
<213> ORGANISM: Artificial Sequence
<220> FEATURE:
<223> OTHER INFORMATION: Artificially synthesized sequence s2 (5-11)

<400> SEQUENCE: 39

```
Arg Thr Met Val His Pro Lys
1               5
```

<210> SEQ ID NO 40
<211> LENGTH: 8
<212> TYPE: PRT
<213> ORGANISM: Artificial Sequence
<220> FEATURE:
<223> OTHER INFORMATION: Artificially synthesized sequence s2 (8-15)

<400> SEQUENCE: 40

```
Val His Pro Lys Pro Ala Gln Pro
1               5
```

<210> SEQ ID NO 41
<211> LENGTH: 8
<212> TYPE: PRT
<213> ORGANISM: Artificial Sequence
<220> FEATURE:
<223> OTHER INFORMATION: Artificially synthesized sequence s2 (r1-8)

<400> SEQUENCE: 41

```
Val Met Thr Arg Pro Leu Arg Ala
1               5
```

<210> SEQ ID NO 42
<211> LENGTH: 7
<212> TYPE: PRT
<213> ORGANISM: Artificial Sequence
<220> FEATURE:
<223> OTHER INFORMATION: Influenza virus infection-inhibiting peptide s2 (1-7)

<400> SEQUENCE: 42

Ala Arg Leu Pro Arg Thr Met
1               5

<210> SEQ ID NO 43
<211> LENGTH: 6
<212> TYPE: PRT
<213> ORGANISM: Artificial Sequence
<220> FEATURE:
<223> OTHER INFORMATION: Influenza virus infection-inhibiting peptide
      s2 (1-6)

<400> SEQUENCE: 43

Ala Arg Leu Pro Arg Thr
1               5

<210> SEQ ID NO 44
<211> LENGTH: 5
<212> TYPE: PRT
<213> ORGANISM: Artificial Sequence
<220> FEATURE:
<223> OTHER INFORMATION: Influenza virus infection-inhibiting peptide
      s2 (1-5)

<400> SEQUENCE: 44

Ala Arg Leu Pro Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Artificially synthesized sequence s2 (2-8)

<400> SEQUENCE: 45

Arg Leu Pro Arg Thr Met Val
1               5

<210> SEQ ID NO 46
<211> LENGTH: 6
<212> TYPE: PRT
<213> ORGANISM: Artificial Sequence
<220> FEATURE:
<223> OTHER INFORMATION: Artificially synthesized sequence s2 (3-8)

<400> SEQUENCE: 46

Leu Pro Arg Thr Met Val
1               5

<210> SEQ ID NO 47
<211> LENGTH: 5
<212> TYPE: PRT
<213> ORGANISM: Artificial Sequence
<220> FEATURE:
<223> OTHER INFORMATION: Artificially synthesized sequence s2 (4-8)

<400> SEQUENCE: 47

Pro Arg Thr Met Val
1               5

<210> SEQ ID NO 48
<211> LENGTH: 5
<212> TYPE: PRT
<213> ORGANISM: Artificial Sequence
<220> FEATURE:
<223> OTHER INFORMATION: Influenza virus infection-inhibiting peptide
      s2(1-5) (general formula)
<220> FEATURE:
<221> NAME/KEY: MISC_FEATURE
<222> LOCATION: (1)..(1)
<223> OTHER INFORMATION: Xaa = Gly, Ala, Val, Leu, or Ile
<220> FEATURE:
<221> NAME/KEY: MISC_FEATURE
<222> LOCATION: (2)..(2)
<223> OTHER INFORMATION: Xaa = Arg or Lys
<220> FEATURE:
<221> NAME/KEY: MISC_FEATURE
<222> LOCATION: (3)..(3)
<223> OTHER INFORMATION: Xaa = Gly, Ala, Val, Leu, or Ile
<220> FEATURE:
<221> NAME/KEY: MISC_FEATURE
<222> LOCATION: (4)..(4)
<223> OTHER INFORMATION: Xaa = Pro, Ala, or Gly
<220> FEATURE:
<221> NAME/KEY: MISC_FEATURE
<222> LOCATION: (5)..(5)
<223> OTHER INFORMATION: Xaa =  Arg or Lys

<400> SEQUENCE: 48

Xaa Xaa Xaa Xaa Xaa
1               5

<210> SEQ ID NO 49
<211> LENGTH: 7
<212> TYPE: PRT
<213> ORGANISM: Artificial Sequence
<220> FEATURE:
<223> OTHER INFORMATION: Influenza virus infection-inhibiting peptide
      s2 (2-8)(general formula)
<220> FEATURE:
<221> NAME/KEY: MISC_FEATURE
<222> LOCATION: (1)..(1)
<223> OTHER INFORMATION: Xaa = Arg or Lys
<220> FEATURE:
<221> NAME/KEY: MISC_FEATURE
<222> LOCATION: (2)..(2)
<223> OTHER INFORMATION: Xaa = Gly, Ala, Val, Leu, or Ile
<220> FEATURE:
<221> NAME/KEY: MISC_FEATURE
<222> LOCATION: (3)..(3)
<223> OTHER INFORMATION: Xaa = Pro, Ala, or Gly
<220> FEATURE:
<221> NAME/KEY: MISC_FEATURE
<222> LOCATION: (4)..(4)
<223> OTHER INFORMATION: Xaa = Arg or Lys
<220> FEATURE:
<221> NAME/KEY: MISC_FEATURE
<222> LOCATION: (5)..(5)
<223> OTHER INFORMATION: Xaa = Ser or Thr
<220> FEATURE:
<221> NAME/KEY: MISC_FEATURE
<222> LOCATION: (6)..(6)
<223> OTHER INFORMATION: Xaa = Cys or Met
<220> FEATURE:
<221> NAME/KEY: MISC_FEATURE
<222> LOCATION: (7)..(7)
<223> OTHER INFORMATION: Xaa = Gly, Ala, Val, Leu, or Ile

<400> SEQUENCE: 49

Xaa Xaa Xaa Xaa Xaa Xaa Xaa
1               5

<210> SEQ ID NO 50
<211> LENGTH: 15
<212> TYPE: PRT
<213> ORGANISM: Artificial Sequence
<220> FEATURE:
<223> OTHER INFORMATION: Hemagglutinin-binding peptide s2(general
      formula)
<220> FEATURE:
<221> NAME/KEY: MISC_FEATURE
<222> LOCATION: (1)..(1)
<223> OTHER INFORMATION: Xaa = Gly, Ala, Val, Leu, or Ile
<220> FEATURE:
<221> NAME/KEY: MISC_FEATURE
<222> LOCATION: (2)..(2)
<223> OTHER INFORMATION: Xaa = Arg or Lys
<220> FEATURE:
<221> NAME/KEY: MISC_FEATURE
<222> LOCATION: (3)..(3)
<223> OTHER INFORMATION: Xaa = Gly, Ala, Val, Leu, or Ile
<220> FEATURE:
<221> NAME/KEY: MISC_FEATURE
<222> LOCATION: (4)..(4)
<223> OTHER INFORMATION: Xaa = Pro, Ala, or Gly
<220> FEATURE:
<221> NAME/KEY: MISC_FEATURE
<222> LOCATION: (5)..(5)
<223> OTHER INFORMATION: Xaa = Arg or Lys
<220> FEATURE:
<221> NAME/KEY: MISC_FEATURE
<222> LOCATION: (6)..(6)
<223> OTHER INFORMATION: Xaa = Ser or Thr
<220> FEATURE:
<221> NAME/KEY: MISC_FEATURE
<222> LOCATION: (7)..(7)
<223> OTHER INFORMATION: Xaa = Cys or Met
<220> FEATURE:
<221> NAME/KEY: MISC_FEATURE
<222> LOCATION: (8)..(8)
<223> OTHER INFORMATION: Xaa = Gly, Ala, Val, Leu, or Ile
<220> FEATURE:
<221> NAME/KEY: MISC_FEATURE
<222> LOCATION: (10)..(10)
<223> OTHER INFORMATION: Xaa = Pro. Ala, or Gly
<220> FEATURE:
<221> NAME/KEY: MISC_FEATURE
<222> LOCATION: (11)..(11)
<223> OTHER INFORMATION: Xaa = Arg or Lys
<220> FEATURE:
<221> NAME/KEY: MISC_FEATURE
<222> LOCATION: (12)..(12)
<223> OTHER INFORMATION: Xaa = Pro, Ala, or Gly
<220> FEATURE:
<221> NAME/KEY: MISC_FEATURE
<222> LOCATION: (13)..(13)
<223> OTHER INFORMATION: Xaa = Gly, Ala, Val, Leu, or Ile
<220> FEATURE:
<221> NAME/KEY: MISC_FEATURE
<222> LOCATION: (14)..(14)
<223> OTHER INFORMATION: Xaa =  Gln or Asn
<220> FEATURE:
<221> NAME/KEY: MISC_FEATURE
<222> LOCATION: (15)..(15)
<223> OTHER INFORMATION: Xaa =  Pro, Ala, or Gly

<400> SEQUENCE: 50

Xaa Xaa Xaa Xaa Xaa Xaa Xaa Xaa His Xaa Xaa Xaa Xaa Xaa Xaa
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Hemagglutinin-binding peptide pVIII

<400> SEQUENCE: 51

Ala Glu Gly Asp Asp Pro Ala Lys Ala Ala Phe Asp Ser Leu Gln
1               5                   10                  15

<210> SEQ ID NO 52
<211> LENGTH: 4
<212> TYPE: PRT
<213> ORGANISM: Artificial Sequence
<220> FEATURE:
<223> OTHER INFORMATION: Influenza virus infection-inhibiting peptide
      s2(1-4)

<400> SEQUENCE: 52

Ala Arg Leu Pro
1

<210> SEQ ID NO 53
<211> LENGTH: 4
<212> TYPE: PRT
<213> ORGANISM: Artificial Sequence
<220> FEATURE:
<223> OTHER INFORMATION: Artificially synthesized sequence s2(1-4)P4A

<400> SEQUENCE: 53

Ala Arg Leu Ala
1

<210> SEQ ID NO 54
<211> LENGTH: 3
<212> TYPE: PRT
<213> ORGANISM: Artificial Sequence
<220> FEATURE:
<223> OTHER INFORMATION: Artificially synthesized sequence s2(1-3)

<400> SEQUENCE: 54

Ala Arg Leu
1

<210> SEQ ID NO 55
<211> LENGTH: 2
<212> TYPE: PRT
<213> ORGANISM: Artificial Sequence
<220> FEATURE:
<223> OTHER INFORMATION: Artificially synthesized sequence s2(1-2)

<400> SEQUENCE: 55

Ala Arg
1

<210> SEQ ID NO 56
<211> LENGTH: 5
<212> TYPE: PRT
<213> ORGANISM: Artificial Sequence
<220> FEATURE:
<223> OTHER INFORMATION: Influenza virus infection-inhibiting peptide
s2(r1-5)

<400> SEQUENCE: 56

Arg Pro Leu Arg Ala
1 5

<210> SEQ ID NO 57
<211> LENGTH: 4
<212> TYPE: PRT
<213> ORGANISM: Artificial Sequence
<220> FEATURE:
<223> OTHER INFORMATION: Influenza virus infection-inhibiting peptide
s2(r1-4)

<400> SEQUENCE: 57

Pro Leu Arg Ala
1

<210> SEQ ID NO 58
<211> LENGTH: 4
<212> TYPE: PRT
<213> ORGANISM: Artificial Sequence
<220> FEATURE:
<223> OTHER INFORMATION: Influenza virus infection-inhibiting peptide
s2(1-4)(general formula)
<220> FEATURE:
<221> NAME/KEY: misc_feature
<222> LOCATION: (1)..(1)
<223> OTHER INFORMATION: Xaa = Gly, Ala, Val, Leu, or Ile
<220> FEATURE:
<221> NAME/KEY: misc_feature
<222> LOCATION: (2)..(2)
<223> OTHER INFORMATION: Xaa = Arg or Lys
<220> FEATURE:
<221> NAME/KEY: misc_feature
<222> LOCATION: (2)..(2)
<223> OTHER INFORMATION: Xaa = Arg or Lys
<220> FEATURE:
<221> NAME/KEY: misc_feature
<222> LOCATION: (3)..(3)
<223> OTHER INFORMATION: Xaa = Gly, Ala, Val, Leu, or Ile
<220> FEATURE:
<221> NAME/KEY: misc_feature
<222> LOCATION: (4)..(4)
<223> OTHER INFORMATION: Xaa = Pro, Ala, or Gly

<400> SEQUENCE: 58

Xaa Xaa Xaa Xaa
1

<210> SEQ ID NO 59
<211> LENGTH: 5
<212> TYPE: PRT
<213> ORGANISM: Artificial Sequence
<220> FEATURE:
<223> OTHER INFORMATION: Hemagglutinin-binding peptide s2(r1-5)(general
formula)
<220> FEATURE:
<221> NAME/KEY: misc_feature
<222> LOCATION: (1)..(1)
<223> OTHER INFORMATION: Xaa = Arg or Lys
<220> FEATURE:
<221> NAME/KEY: misc_feature
<222> LOCATION: (2)..(2)
<223> OTHER INFORMATION: Xaa = Pro, Ala, or Gly
<220> FEATURE:
<221> NAME/KEY: misc_feature
<222> LOCATION: (3)..(3)
<223> OTHER INFORMATION: Xaa = Gly, Ala, Val, Leu, or Ile
<220> FEATURE:
<221> NAME/KEY: misc_feature
<222> LOCATION: (4)..(4)
<223> OTHER INFORMATION: Xaa = Arg or Lys
<220> FEATURE:
<221> NAME/KEY: misc_feature
<222> LOCATION: (5)..(5)
<223> OTHER INFORMATION: Xaa = Gly, Ala, Val, Leu, or Ile

<400> SEQUENCE: 59

Xaa Xaa Xaa Xaa Xaa
1 5

<210> SEQ ID NO 60
<211> LENGTH: 4
<212> TYPE: PRT
<213> ORGANISM: Artificial Sequence
<220> FEATURE:
<223> OTHER INFORMATION: Hemagglutinin-binding peptide s2(r1-4)(general
formula)
<220> FEATURE:
<221> NAME/KEY: misc_feature
<222> LOCATION: (1)..(1)
<223> OTHER INFORMATION: Xaa=Pro, Ala, or Gly
<220> FEATURE:
<221> NAME/KEY: misc_feature
<222> LOCATION: (2)..(2)
<223> OTHER INFORMATION: Xaa=Gly, Ala, Val, Leu, or Ile
<220> FEATURE:
<221> NAME/KEY: misc_feature
<222> LOCATION: (3)..(3)
<223> OTHER INFORMATION: Xaa=Arg or Lys
<220> FEATURE:
<221> NAME/KEY: misc_feature -continued

```
<222> LOCATION: (4)..(4)
<223> OTHER INFORMATION: Xaa=Gly, Ala, Val, Leu, or Ile

<400> SEQUENCE: 60

Xaa Xaa Xaa Xaa
1


<210> SEQ ID NO 61
<211> LENGTH: 4
<212> TYPE: PRT
<213> ORGANISM: Artificial Sequence
<220> FEATURE:
<223> OTHER INFORMATION: Influenza virus infection-inhibiting peptide

<400> SEQUENCE: 61

Arg Leu Pro Arg
1


<210> SEQ ID NO 62
<211> LENGTH: 15
<212> TYPE: PRT
<213> ORGANISM: Artificial Sequence
<220> FEATURE:
<223> OTHER INFORMATION: Hemagglutinin-binding peptide H3G-1

<400> SEQUENCE: 62

Gly Leu Ala Met Ala Pro Ser Val Gly His Val Arg Gln His Gly
1               5                   10                  15
```

INFLUENZA INFECTION-INHIBITING PEPTIDE, INFLUENZA VIRUS INFECTION INHIBITOR, LIPOSOME, AND INFLUENZA PREVENTIVE/THERAPEUTIC AGENT

CROSS-REFERENCE TO RELATED APPLICATIONS

The present application is the U.S. National Stage of International Application No. PCT/JP2007/054452, filed Mar. 7, 2007, which claims the benefit of Japanese Application Serial No. JP 2006-068020, filed Mar. 13, 2006.

TECHNICAL FIELD

The present invention relates to influenza infection-inhibiting peptides which inhibit influenza virus infection; influenza virus infection inhibitors which inhibit influenza virus infection; liposomes containing the influenza infection-inhibiting peptide; and influenza preventive/therapeutic agents containing the influenza virus infection-inhibiting peptide.

BACKGROUND ART

Influenza viruses have two kinds of glycoproteins in their envelope membranes: hemagglutinin (HA) and sialidase (neuraminidase), each of which plays an important role in establishment of viral infection and viral budding from a host cell, respectively. Hemagglutinin recognizes a sialic acid-containing sugar chain generally present on the cell membrane of a host (a human or an animal other than a human, such as a mammal, a bird, a reptile, a fish, an amphibian, etc.) as a receptor to which it specifically binds, leading to intracellular endocytosis of the influenza virus. On the other hand, neuraminidase, a receptor-destroying enzyme, serves to cleave sialic acid residues on the host cell membrane or virus' own membrane when the viral particles bud or are released from the host cell.

Hemagglutinin, involved in the first step of influenza virus infection, has various subtypes based on the diversity of amino acid sequences of the antigen-determining regions (A-E) which are highly mutatable. Since amino acid sequence homologies among hemagglutinin subtypes are 25 to 75%, it is extremely difficult to develop an influenza vaccine based on antigenicity. On the other hand, the so-called receptor binding pocket region which binds to the receptor of a host cell is comparatively less mutatable and its three-dimensional structure is well conserved (Y. Suzuki, Prog. Lipid. Res., 33, 429 (1994). Therefore, to prevent influenza virus infection, if an agent inhibits the function of hemagglutinin, which is to contribute to establishment of infection, by specifically binding to it, broad effect will be expected in prevention of influenza virus infection, and thus development of such an agent has been demanded.

For example, based on the fact that hemagglutinin recognizes and binds to a sialic acid-containing sugar chain of a host receptor, a variety of hemagglutinin-binding sugar analogs have been obtained to date by using the technique of screening for sugar analogs specifically binding to the binding site of hemagglutinin (R. Roy, et al., J. Chem. Soc., Chem. Commun., 1869 (1993); M. Mammen, et al., J. Med. Chem., 38, 4179 (1995); T. Sato, et al., Chem. Lett., 145 (1999); M. Itzstein, et al., Nature, 363, 418 (1993)).

Another technique has been developed for preparing an antibody (anti-idiotype antibody) against the antigenic type (idiotype) of the antigen-binding site of a monoclonal antibody against the hemagglutinin receptor sugar chain. The principle applied here is that, in place of the three-dimensional structures of sialic acid and sialo-sugar chains acting as hemagglutinin receptors, the amino acid sequence of the supervariable region of an antiidiotype antibody which, in spatial configuration, resembles the three-dimensional structures, is constructed and caused to mimic the hemagglutinin receptors on host cells (Yasuo Suzuki, "Virus Kansen to Tosa" (Viral Infection and Sugar Chain), Nikkei Science supplemental issue "Tosa to Saibo" (Sugar Chain and Cell), pp. 89-101, October 1994].

However, although the receptor binding pocket region is comparatively less mutatable and its three-dimensional structure is well conserved, the region is specific to the subtype of hemagglutinin and its binding constant is not so high. Therefore, development of agents acting on influenza viruses in general, regardless of the subtype, has been awaited.

Then, 15-residue oligopeptides were screened by the phage display method for those which prevent influenza virus infection by binding to hemagglutinin, and 11 types (WO00/59932) and 3 types (Japanese Laid-Open Application No. 2002-284798; T. Sato, et al., Peptide Science 2001, 329 (2002)) of oligopeptides were identified (WO00/59932).

DISCLOSURE OF THE INVENTION

Problems to be Solved by the Invention

However, the titer of the phage library used for screening performed in WO00/59932 and Japanese Laid-Open Application No. 2002-284798 was $2.5\times10^8$, which is far below $20^{15}$ ($=3.3\times10^{19}$), the total number of 15-amino acid residue sequences. The existence of peptides having a higher affinity for hemagglutinin than these oligopeptides was suspected.

Thus, the present invention has been made in order to provide, by screening for a larger number peptides, peptides having high affinity for hemagglutinin or a peptide having high inhibitory activity against influenza virus infection, and further to provide pharmaceutical compositions containing such a peptide having a high affinity for hemagglutinin or a peptide having a high inhibitory activity against influenza virus infection.

Means for Solving the Problem

The peptide according to the present invention is a peptide having 4 to 14 residues, including the amino acid sequence of $X_1X_2X_3X_4$ (SEQ ID NO: 58), wherein $X_1$ is alanine, glycine, isoleucine, valine, or leucine; $X_2$ is arginine or lysine; $X_3$ is alanine, glycine, isoleucine, valine, or leucine; and $X_4$ is proline, alanine, or glycine. It is preferred that $X_4$ is proline.

Further, the peptide according to the present invention is a peptide having 4 to 14 residues, being a part of SEQ ID NO: 3 and including the amino acid sequence of $X_1X_2X_3X_4$ (SEQ ID NO: 58), wherein $X_1$ is alanine, glycine, isoleucine, valine, or leucine; $X_2$ is arginine or lysine; $X_3$ is alanine, glycine, isoleucine, valine, or leucine; and $X_4$ is proline, alanine, or glycine. It is preferred that $X_4$ is proline.

Further, the peptide according to the present invention is a peptide having 5 to 14 residues, including the amino acid sequence of $X_1X_2X_3X_4X_5$ (SEQ ID NO: 48), wherein $X_1$ is alanine, glycine, isoleucine, valine, or leucine; $X_2$ is arginine or lysine; $X_3$ is alanine, glycine, isoleucine, valine, or leucine; $X_4$ is proline, alanine, or glycine; and $X_5$ is arginine or lysine. It is preferred that $X_4$ is proline.

Further, the peptide according to the present invention is a peptide having 5 to 14 residues, being a part of SEQ ID NO: 3 and including the amino acid sequence of $X_1X_2X_3X_4X_5$ (SEQ ID NO: 48) wherein $X_1$ is alanine, glycine, isoleucine, valine, or leucine; $X_2$ is arginine or lysine; $X_3$ is alanine, glycine, isoleucine, valine, or leucine; $X_4$ is proline, alanine, or glycine; and $X_5$ is arginine or lysine. It is preferred that $X_4$ is proline.

The peptide according to the present invention is the peptide of 5 to 14 residues, being a part of the sequence of $X_1X_2X_3X_4X_5X_6X_7X_8HX_9X_{10}X_{11}X_{12}X_{13}X_{14}$ (SEQ ID NO: 50) and including the amino acid sequence of $X_1X_2X_3X_4X_5$ (SEQ ID NO: 48) wherein $X_1$ is alanine, glycine, isoleucine, valine, or leucine; $X_2$ is arginine or lysine; $X_3$ is alanine, glycine, isoleucine, valine, or leucine; $X_4$ is proline, alanine, or glycine; $X_5$ is arginine or lysine; $X_6$ is serine or threonine; $X_7$ is cysteine or methionine; $X_8$ is alanine, glycine, isoleucine, valine, or leucine; $X_9$ is proline, alanine, or glycine; $X_{10}$ is arginine or lysine; $X_{11}$ is proline, alanine, or glycine; $X_{12}$ is alanine, glycine, isoleucine, valine, or leucine; $X_{13}$ is glutamine or asparagine; and $X_{14}$ is proline, alanine, or glycine. It is preferred that each of $X_4$, $X_9$, $X_{11}$, and $X_{14}$ is proline.

Further, the peptide according to the present invention has the amino acid sequence selected from a group consisting of SEQ ID NOs: 38, 42 to 44, and 52.

The peptide according to the present invention has an amino acid sequence selected from a group consisting of SEQ ID NOs: 38, 42 to 44, and 52 from/to which one or several amino acid residues are substituted, deleted, or added, and has inhibitory activity against influenza virus infection.

Preferably, the aforementioned peptide is alkylated.

Further, the peptide according to the present invention is a peptide having 4 to 14 residues, including the amino acid sequence of $X_4X_3X_2X_1$ (SEQ ID NO: 60), wherein $X_4$ is proline, alanine, or glycine; $X_3$ is alanine, glycine, isoleucine, valine, or leucine; $X_2$ is arginine or lysine; and $X_1$ is alanine, glycine, isoleucine, valine, or leucine. It is preferred that $X_4$ is proline.

Further, the peptide according to the present invention is a peptide having 5 to 14 residues, including the amino acid sequence of $X_5X_4X_3X_2X_1$ (SEQ ID NO: 59), wherein $X_5$ is arginine or a lysine, $X_4$ is proline, alanine, or glycine; $X_3$ is alanine, glycine, isoleucine, valine, or leucine; $X_2$ is arginine or lysine; and $X_1$ is alanine, glycine, isoleucine, valine, or leucine. It is preferred that $X_4$ is proline.

Further, the peptide according to the present invention has the amino acid sequence of SEQ ID NO: 56 or 57.

The peptide according to the present invention has an amino acid sequence of either SEQ ID NO: 56 or 57 from/to which one or several amino acid residues are substituted, deleted, or added, and has inhibitory activity against influenza virus infection.

Preferably, each of the aforementioned peptide is alkylated.

The influenza virus infection-inhibitor according to the present invention contains the peptide of any one of the aforementioned peptides as an active ingredient. This influenza virus infection inhibitor inhibits infections of both an influenza virus having hemagglutinin H1 and an influenza virus having hemagglutinin H3.

The influenza preventive/therapeutic agent according to the present invention contains the peptide of any one of the aforementioned peptides as an active ingredient. This influenza preventive/therapeutic agent is effective for infections of both an influenza virus having hemagglutinin H1 and an influenza virus having hemagglutinin H3.

The DNA according to the present invention encodes any one of the aforementioned peptides.

The expression vector according to the present invention includes the aforementioned DNA.

Further, the cell according to the present invention is introduced with the aforementioned expression vector and secretes any one of the aforementioned peptides.

The liposome according to the present invention contains the peptide of any one of the aforementioned peptides. The peptide in this liposome is preferably alkylated.

The influenza virus infection inhibitor according to the present invention is an influenza virus infection inhibitor containing any one of the aforementioned peptides, in which the peptide is modified so as to have amphiphilicity and form a peptide aggregate. The modification in the influenza virus infection inhibitor is preferably alkylation.

The peptide aggregate according to the present invention refers to the aforementioned peptide aggregate.

The peptide according to the present invention has the amino acid sequence of $X_2X_3X_4X_5X_6X_7X_8$ (SEQ ID NO 49:s2(2-8) (general formula)), wherein $X_2$ is arginine or lysine; $X_3$ is alanine, glycine, isoleucine, valine, or leucine; $X_4$ is proline, alanine, or glycine; $X_5$ is arginine or lysine; $X_6$ is serine or threonine; $X_7$ is cysteine or methionine; and $X_8$ is alanine, glycine, isoleucine, valine, or leucine. It is preferred that $X_4$ is proline.

Further, the peptide according to the present invention has an amino acid sequence of $X_2X_3X_4X_5X_6X_7X_8$ (SEQ ID No: 49) from/to which one or several amino acid residues are substituted, deleted, or added, and has inhibitory activity against influenza virus infection. It is preferred that $X_4$ is proline.

Preferably, the aforementioned peptide is alkylated.

The influenza virus infection inhibitor according to the present invention contains anyone of the aforementioned peptides as an active ingredient. It should be noted that this influenza virus infection inhibitor inhibits infection of an influenza virus having hemagglutinin H1.

PREFERRED EMBODIMENTS FOR CARRYING OUT THE INVENTION

Figure 1:
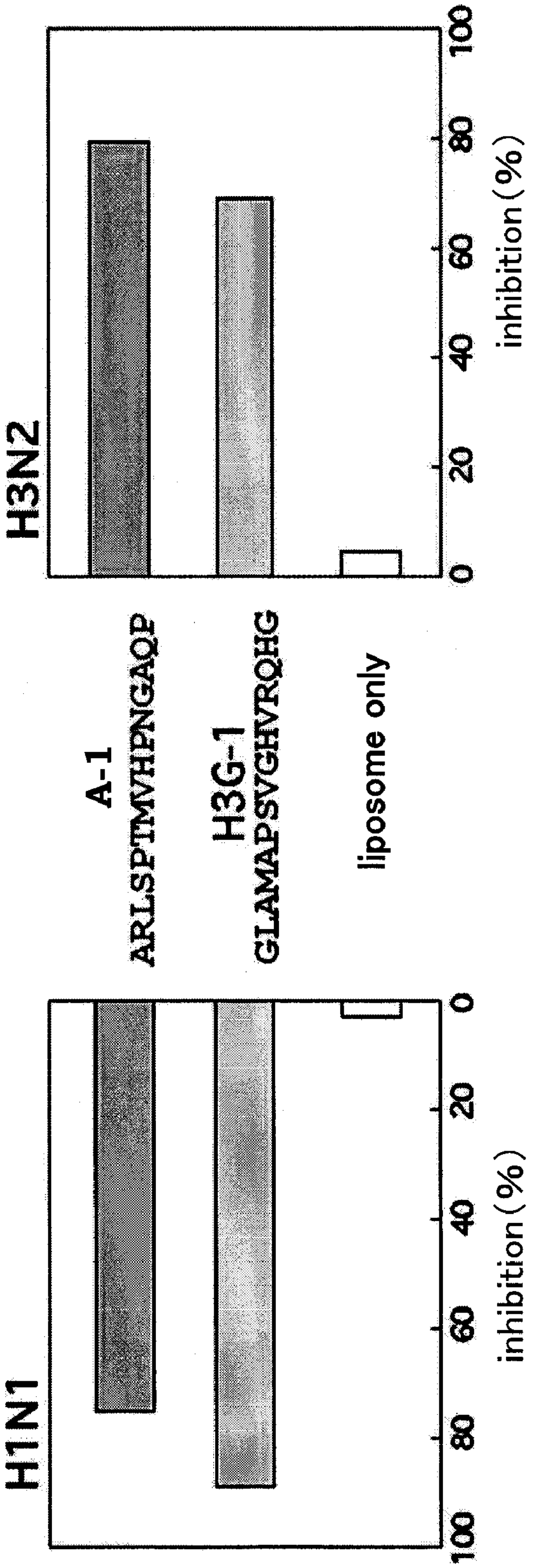
FIG. 1 shows a graph comparing the binding activities of A-1 (SEQ ID NO: 1) and H3G-1 (SEQ ID NO: 62) to hemagglutinin, using ELISA in an example according to the present invention.

Unless otherwise explained, methods described in standard sets of protocols such as J. Sambrook and E. F. Fritsch & T. Maniatis (Ed.), "Molecular Cloning, a Laboratory Manual (3rd edition), Cold Spring Harbor Press and Cold Spring Harbor, N.Y. (1989); and F. M. Ausubel, R. Brent, R. E. Kingston, D. D. Moore, J. G. Seidman, J. A. Smith, and K. Struhl (Ed.), "Current Protocols in Molecular Biology," John Wiley & Sons Ltd., or alternatively, their modified/changed methods are used. When using commercial reagent kits and measuring apparatus, unless otherwise explained, protocols attached to them are used.

The object, characteristics, and advantages of the present invention as well as the idea thereof will be apparent to those skilled in the art from the descriptions given herein. It is to be understood that the embodiments and specific examples of the invention described herein below are to be taken as preferred examples of the present invention. These descriptions are only for illustrative and explanatory purposes and are not intended to limit the invention to these embodiments or examples. It is further apparent to those skilled in the art that various changes and modifications may be made based on the descriptions given herein within the intent and scope of the present invention disclosed herein.

==Hemagglutinin-Binding Peptides==

Table 1 shows the amino acid sequences of the hemagglutinin-binding peptides as used herein.

In this list, peptide A-1 having the amino acid sequence of SEQ ID NO:1 has the highest binding activity among the hemagglutinin-binding peptides identified to date (see WO00/59932 and the Specification and Examples of Japanese Laid-Open Application No. 2002-284798) However, the polypeptides having the amino acid sequences of SEQ ID NOs: 2 to 7, 9 to 10, and 12 to 18 have even higher binding activity to hemagglutinin than A-1, as shown in the Examples. Further, as shown in the Examples, these polypeptides having the amino acid sequences of SEQ ID NOs: 2 to 7, 9 to 10, and 12 to 18 bind to both of hemagglutinins H1 and H3.

It should be noted that the hemagglutinin-binding peptides according to the present invention may have an amino acid sequence in which one or several amino acid residues are substituted, deleted, or added, from/to SEQ ID NOs: 2 to 7, 9 to 10, and 12 to 18, and has a high inhibitory activity against hemagglutinin.

While the binding activity of a hemagglutinin-binding peptide to hemagglutinin can be measured by, for example, ELISA, it may be measured by any other technique, such as RIA, EIA, Western blotting, or the like, as long as it can measure quantitatively protein-protein interaction.

TABLE 1

| Name | Seq. No. | a. a. seq. | Seq. No. | Nuc. seq. |
|---|---|---|---|---|
| A-1 | 1 | ARLSPTMVHPNSAQP | 19 | GCGCGTTTGTCTCCTACTATGGTTCATCCTAATGGTGCGCAGCCT |
| s-1 | 2 | ARLSPNMVHLNPAQP | 20 | GCGCGTTTGTCGCCTAATATGGTTCATCTTAATCCTGCGCAGCCT |
| s-2 | 3 | ARLPRTMVHPKPAQP | 21 | GCGCGTTTGCCTCGTACTATGGTTCATCCTAAACCTGCGCAGCCA |
| s-3 | 4 | ARLSPTMVHPHPAKS | 22 | GCGCGACTGTCTCCTACTATGGTTCATCCTCATCCCGCGAAGTCT |
| e-1 | 5 | ARLPPTMVRPNGPQP | 23 | GCGCGTTTGCCTCCTACTATGGTTCGTCCTAATGGTCCGCAGCCT |
| e-2 | 6 | ARLPPAMVRPNGPQP | 24 | GCGCGTTTGCCTCCTGCTATGGTTCGTCCTAATGGTCCGCAGCCT |
| e-3 | 7 | ARLSPTMVRPIGAQP | 25 | GCACGTTTGTCACCTACTATGGTTCGTCCTATTGGTGCACAGCCT |
| e-4 | 8 | ARLSPTMVHLNGAQP | 26 | GCGCGTTTGTCTCCTACTATGGTTCATCTTAATGGTGCGCAGCCT |
| e-5 | 9 | TRLSHIMVHRNGAQP | 27 | ACGCGTTTGTCTCATATTATGGTTCATCGTAATGGTGCGCAGCCT |
| e-6 | 10 | TRLPPAMVHPNGAQH | 28 | ACGCGTTTGCCTCCTGCTATGGTCCATCCTAATGGAGCCCAGCAT |
| e-7 | 11 | ARLSPTMVHPNGAQH | 29 | GCGCGTTTGTCTCCTACTATGGTCCATCCTAATGGTGCGCAGCAT |
| e-8 | 12 | ARLSPAMVHPNGARL | 30 | GGGCGTTTGTCTCCCGCTATGGTACATCCTAATGGTGCGCGGCTT |
| e-9 | 13 | ARLSPAMVRPNGARP | 31 | CCGCGTTTGTCTCCTGCTATGGTTCGTCCTAATGGTGCGCGGCCT |
| e-10 | 14 | ARLSPTMVHRHGAQP | 32 | GCGCGTTTGTCTCCAACTATGGTTCATCGTCATGGTGCGCAGCCT |
| e-11 | 15 | TRLPPTMIHPNCAQP | 33 | ACTCGTTTGCCTCCTACTATGATTCATCCTAATGGTGCGCAGCCT |
| e-12 | 16 | ARLSPTMVHPRGAQP | 34 | GCGCGTTTGTCTCCTACTATGGTTCATCCTAGAGGTGCTCAGCCT |
| e-13 | 17 | ARLSPTMVHRNGVQP | 35 | GCGCGTTTGTCTCCTACTATGGTTCATCGTAATGGTGTGCAGCCT |
| e-14 | 18 | TRLPPAMARPNSAQP | 36 | ACGCGTTTGCCTCCAGCTATGGCTCGTCCTAATAGCGCACAGCCT |

Nucleotides and amino acids different from those of A-1 are underlined

==Influenza Virus Infection-Inhibiting Peptide==

Table 2 shows the amino acid sequences of the influenza virus infection-inhibiting peptides as used herein.

TABLE 2

| No. | a. a. seq. | Residues |
|---|---|---|
| Seq. No. 3 | ARLPRTMVHPKPAQP | 15 |
| Seq. No. 38 | ARLPRTMV | 8 |
| Seq. No. 42 | ARLPRTM | 7 |
| Seq. No. 43 | ARLPRT | 6 |
| Seq. No. 44 | ARLPR | 5 |
| Seq. No. 52 | ARLP | 4 |
| Seq. No. 56 | RPLRA | 5 |
| Seq. No. 57 | PLRA | 4 |

The influenza virus infection-inhibiting peptides having the amino acid sequences of SEQ ID NOs: 38, 42 to 44, 52, 56, and 57 can strongly inhibit influenza virus infection to host cells, as described in the following Examples.

It should be noted that the influenza virus infection-inhibiting peptides according to the present invention may have an amino acid sequence in which one or several amino acid residues are substituted, deleted, or added, from/to SEQ ID NOs: 38, 42 to 44, 52, 56, and 57 and has inhibitory activity against influenza virus infection.

The inhibition of influenza virus infection to host cells by the influenza virus infection-inhibiting peptide can be measured by, for example, the plaque assay method.

In general, it is known among those skilled in the art that the function of a peptide will not change if a substitution is made within the peptide between amino acids having a side chain of the same property (for example, aliphatic side chains etc.).

Therefore, the peptide having the ARLP (SEQ ID NO: 52) sequence with, for example, a substitution of A by an amino acid having an aliphatic side chain (for example, G, V, L, or I), a substitution of R by an amino acid having a basic side chain (for example, K), and/or a substitution of L by an amino acid having aliphatic side chain (for example, G, V, A, or I), is considered to have similar activity as the peptide having the ARLP (SEQ ID NO 52) sequence. Moreover, it is known that, in a general point mutation experiment, a peptide with a substitution of proline by alanine or glycine will possess the activity of the same degree (Teruhiko Matsubara, dissertation, Tokyo Institute of Technology (2000)). Thus, a peptide with a substitution of P by A or G is considered to have similar activity as the peptide having the ARLP (SEQ ID NO: 52) sequence. Such sequences can be represented by the general formula of $X_1X_2X_3X_4$ (SEQ ID NO:58:s2 (1-4) (general formula)), wherein $X_1$ is alanine, glycine, isoleucine, valine, or leucine; $X_2$ is arginine or lysine; $X_3$ is alanine, glycine, isoleucine, valine, or leucine; and $X_4$ is proline, alanine, or glycine. It is preferred that $X_4$ is proline.

This the peptide according to the present invention has 4 to 14 residues, which has the above amino acid sequence (SEQ ID NO: 58).

Similarly, the peptide having the ARLPR (SEQ ID NO: 44) sequence with, for example, a substitution of A by an amino acid having an aliphatic side chain (for example, G, V, L, or I), substitution of R by an amino acid having a basic side chain (for example, K) and/or a substitution of L by an amino acid having aliphatic side chain (for example, G, V, A, or I) is considered to have similar activity as the peptide having the ARLPR (SEQ ID NO: 44) sequence. Moreover, the peptide with a substitution of P by A or G is considered to have similar activity as the peptide having the ARLPR (SEQ ID NO: 44) sequence. Such sequences can be represented by the general formula of $X_1X_2X_3X_4X_5$ (SEQ ID NO 48:s2 (1-5) (general formula)), wherein $X_1$ is alanine, glycine, isoleucine, valine, or leucine; $X_2$ is arginine or lysine; $X_3$ is alanine, glycine, isoleucine, valine, or leucine; $X_4$ is proline, alanine, or glycine; and $X_5$ is arginine or lysine It is preferred that $X_4$ is proline.

Thus the peptide according to the present invention has 5 to 14 residues, which has the above amino acid sequence (SEQ ID NO: 48).

Meanwhile, the amino acid sequence of SEQ ID NO: 3 can be represented by the general formula of $X_1X_2X_3X_4X_5X_6X_7X_8HX_9X_{10}X_{11}X_{12}X_{13}X_{14}$ (SEQ ID NO: 50: s2 (general formula)), wherein $X_1$ is alanine, glycine, isoleucine, valine, or leucine; $X_2$ is arginine or lysine; $X^3$ is alanine, glycine, isoleucine, valine, or leucine; $X_4$ is proline, alanine, or glycine; $X_5$ is arginine or lysine; $X_6$ is serine or threonine; $X_7$ is cysteine or methionine; $X_8$ is alanine, glycine, isoleucine, valine, or leucine; $X_9$ is proline, alanine, or glycine; $X_{10}$ is arginine or lysine; $X_{11}$ is proline, alanine, or glycine; $X_{12}$ is alanine, glycine, isoleucine, valine, or leucine; $X_{13}$ is glutamine or asparagine; and $X_{14}$ is proline, alanine, or glycine. It is preferred that each of $X_4$, $X_9$, $X_{11}$, and $X_{14}$ is proline.

Therefore, the peptides according to the present invention may have 4 to 14 residues containing the amino acid sequence (SEQ ID NO 58) as a part of the above-mentioned amino acid sequence (SEQ ID NO 50), and preferably peptides having 4 to 14 residues containing this amino acid sequence (SEQ ID NO: 58) as a part of the SEQ ID NO: 3. In addition, the peptides according to the present invention may have 5 to 14 residues containing the amino acid sequence (SEQ ID NO: 48), and preferably a peptide having 4 to 14 residues containing the amino acid sequence (SEQ ID NO: 48).

Furthermore, the peptide according to the present invention may have an inverted sequence of the ARLPR (SEQ ID NO: 44) sequence or the ARLP (SEQ ID NO: 52) sequence. Thus, the RPLRA (SEQ ID NO: 56) sequence, which is a inverted sequence of the ARLPR (SEQ ID NO: 44) sequence, or the PLRA (SEQ ID NO: 57) sequence, which is a inverted sequence of the ARLP (SEQ ID NO 52) sequence, with, for example, a substitution of A by an amino acid having an aliphatic side chain (for example, G, V, L, or I), a substitution of R by an amino acid having a basic side chain (for example, K), and/or a substitution of L by an amino acid having aliphatic side chain (for example, G, V, A, or I), is considered to have similar activity as the peptide having the RPLRA (SEQ ID NO: 56) sequence or the PLRA (SEQ ID NO: 57) sequence. Moreover, the peptide with a substitution of P by A or G is considered to have similar activity as the peptide having the RPLRA (SEQ ID NO: 56) sequence or the PLRA (SEQ ID NO: 57) sequence. Such sequences can be represented by the general formula of $X_5X_4X_3X_2X_1$ (SEQ ID NO 59:s2 (r1-5) (general formula)) or $X_4X_3X_2X^1$ (SEQ ID NO 60:s2 (r1-4) (general formula)), wherein $X_1$ is alanine, glycine, isoleucine, valine, or leucine; $X_2$ is arginine or lysine; $X_3$ is alanine, glycine, isoleucine, valine, or leucine; $X_4$ is proline, alanine, or glycine; and $X_5$ is arginine or lysine. It is preferred that $X_4$ is proline.

==Pharmaceutical Compositions Containing a Hemagglutinin-Binding Peptide and an Influenza Virus Infection-Inhibiting Peptide==

When an influenza virus infects a host cell, hemagglutinin on the influenza virus specifically binds to a receptor of the cell and enters into the cell by using the receptor as a scaffold. The hemagglutinin-binding peptides according to the present invention specifically bind to the hemagglutinin. Due to this binding, the hemagglutinin is prevented from binding to a host cell receptor, and therefore, infection of the influenza virus to the host cell can be inhibited.

Thus, the hemagglutinin-binding peptides according to the present invention can inhibit infection of an influenza virus to a host cell. Further, the influenza virus infection-inhibiting peptides according to the present invention were able to inhibit infection of an influenza virus to a host, as shown in the following Examples. Therefore, the hemagglutinin-binding peptides and the influenza virus infection-inhibiting peptide according to the present invention can suppress influenza virus proliferation in vivo by being administered to a human or a vertebrate other than a human afflicted with influenza. The hemagglutinin-binding peptides and the influenza virus infection-inhibiting peptides can also prevent infection of an influenza virus even if the influenza virus has entered the body, by being administered in advance to the body of a human or a vertebrate other than a human.

Besides these medical uses as described above, the hemagglutinin-binding peptides according to the present invention can also be used as a tool for elucidating hemagglutinin-mediated influenza virus infection and the accompanying various cell functions and biological phenomena.

The influenza virus targeted by the present invention is not particularly limited in types or origins, as long as it has at least either hemagglutinin H1 or hemagglutinin H3, and it may be any one of type A, type B or type C, human isolates, other mammalian isolates such as swine isolates and equine isolates, or avian isolates.

As described above, it is considered that the pharmaceutical compositions containing the hemagglutinin-binding peptide according to the present invention or the influenza virus infection-inhibiting peptide as an active ingredient may include influenza virus infection inhibitors for inhibiting infection of influenza viruses to host cells, as well as influenza therapeutic agents for treating patients afflicted with influenza, and influenza preventive agents to be administered preventively before the patient have been afflicted with influenza. These pharmaceutical compositions can be made as preparations containing as an active ingredient the hemagglutinin-binding peptide or the influenza virus infection-inhibiting peptide, and a pharmaceutically acceptable carrier as necessary, and then administered to influenza virus-infected humans or vertebrates other than humans or administered preventively to uninfected humans or vertebrates other than humans.

The pharmaceutically acceptable carrier to be used herein can be appropriately selected from among the conventional carriers depending on the form of the pharmaceutical composition to be prepared. For example, when a pharmaceutical composition is prepared in the form of an aqueous solution, purified water (sterile water), a physiological buffer solution, glycol, glycerol, or an injectable organic ester, such as olive oil, can be used as the carrier. In addition, the composition can contain a conventionally used stabilizer, recipient, etc.

The mode of administering these pharmaceutical compositions is not particularly limited and may be appropriately determined depending on conditions such as formulations, the patient's age, sex, and others, as well as severity of the illness, etc. Preferred formulations include injections, drops, sprays (aerosol), nasal drops, and inhalations.

The routs of administration can be either oral or parenteral, and specific examples include oral administration, intravenous administration, intrarterial administration, intramuscular administration, intracutaneous administration, intraperitoneal injection, intratracheal administration, inhalation administration, and sublingual administration.

Since human influenza viruses are known to enter the body via the oral cavity or nasal cavity and proliferate mainly in the mucosal epithelium cells of the upper respiratory tract, the agent of the present invention is preferably administered through the administration route such as oral administration, intratracheal administration, oropharynx administration, and inhalation, etc. to a human influenza virus-infected human or a vertebrate other than human. Specifically, by formulating the agent as a spray, spray aerosol, or an inhalation, it can be administered through the administration route such as oral administration, intratracheal administration, oropharynx administration, and inhalation, thereby making it possible to directly inhibit infection of an influenza virus to respiratory epithelium cells.

The daily dose of these pharmaceutical compositions can be appropriately changed depending on the patient's symptom, age, body weight, sex, duration of treatment, therapeutic effect, mode of administration, etc., and is not limited as long as influenza infection can be inhibited with inevitable side effects within an acceptable range. The preparation may be administered as one dose a day, as well as multiple doses a day.

These pharmaceutical compositions may be used alone or in combination with other agents (for example, another antiviral agent, an anti-inflammatory agent, a symptom-relieving agent, etc.).

The agent can also be used, when influenza vaccines cannot be used, e.g., on high-risk patients who can potentially develop influenza before the effect of the vaccine is exhibited, on patients in whom a sufficient effect of influenza vaccine is not exhibited because of immunodeficiency or the like, and on patients in whom vaccination is contraindicated.

In addition, when administered orally to vertebrates other than humans, the agent can be taken by mixing with drinking water or feed.

==Methods for Producing the Hemagglutinin-Binding Peptide and Influenza Virus Infection-Inhibiting Peptide==

The hemagglutinin-binding peptides or influenza virus infection-inhibiting peptides according to the present invention can be chemosynthetically produced in accordance with the conventional method: for example, it can be produced by peptide synthesis using the conventional liquid-phase and solid-phase methods. More specifically, peptide synthesis may be performed by using methods such as the stepwise elongation method in which individual amino acids are serially bound one by one based on the amino acid sequence information as described above, thereby elongating the chain; and the fragment condensation method in which fragments each consisting of several amino acids are synthesized in advance and these fragments are subjected to coupling reaction.

The condensation to be adopted in the aforementioned peptide synthesis can also be performed by following various known methods. Specific methods can be exemplified by the azide method, mixed acid anhydride method, DCC method, active ester method, redox method, diphenylphosphoryl azide (DPPA) method, DCC+additive (1-hydroxybenzotriazole, N-hydroxysuccinimide, N-hydroxy-5-norbornene-2,3-dicarboximide, or the like) method, Woodward method, etc.

Solvents which may be used in these methods can also be appropriately selected from among the common solvents well known to be used in peptide condensation reactions of this kind. Examples of the solvent include dimethylformamide (DMF), dimethyl sulfoxide (DMSO), hexaphosphoramide, dioxane, tetrahydrofuran (THF), ethyl acetate, and mixtures of these solvents.

In performing the above-described peptide synthesis reactions, the carboxyl groups of amino acids or peptides not involved in the reactions can be generally protected by esterification, for example, by forming a lower alkyl ester (e.g., methyl ester, ethyl ester, tert-butyl ester, or the like) or an aralkyl ester (e.g., benzyl ester, p-methoxybenzyl ester, p-nitrobenzyl ester, or the like). Functional groups in a side chain of amino acids (e.g., Tyr) can be protected with, e.g. an acetyl group, a benzyl group, a benzyloxycarbonyl group, tert-butyl, or the like, although such protection is not always required. In addition, the guanidino group of Arg, for example, can be protected with a suitable protective group such as a nitro group, a tosyl group, 2-methoxybenzenesulfonyl group, methylene-2-sulfonyl group, a benzyloxycarbonyl group, an isobornyloxycarbonyl group, an adamantyloxycarbonyl group, or the like. Deprotection of the aforementioned protected amino acids, peptides, and the peptide finally obtained in the present invention, can also be performed by the conventionally used methods, such as catalytic reduction or other method using liquid ammonia/sodium, hydrogen fluoride, hydrogen bromide, hydrogen chloride, trifluoroacetic acid, acetic acid, formic acid, methanesulfonic acid, or the like.

The peptide thus prepared can be appropriately purified by the conventional method commonly used in the field of peptide chemistry, such as ion-exchange resin chromatography, partition chromatography, gel chromatography, affinity chromatography, high performance liquid chromatography (HPLC), countercurrent distribution, or the like.

Alternatively, DNA encoding the aforementioned hemagglutinin-binding peptide or influenza virus infection-inhibiting peptide may be prepared, incorporated into an expression vector, and introduced into eukaryotic cells such as cultured cells, or prokaryotic cells such as *Escherichia coli*; and the peptide expressed in the cells may be purified. The expression vector is appropriately selected depending on the host cell to be introduced. Construction of a vector, including incorporation of a DNA encoding the peptide, introduction into host cells, expression in the cells, and preparation of extract of the cells, can be performed in accordance with the conventional method using molecular biological techniques. The peptide to be produced can be purified from the extract by the above-described conventional method commonly used in the field of peptide chemistry.

DNA encoding the hemagglutinin-binding peptide or influenza virus infection-inhibiting peptide to which a tag (e.g., a His tag, a Flag tag, a GST tag, etc.) is added may be prepared and expressed in host cells in the same manner as above. By using the tag, the peptide with the tag can be purified through an affinity column or the like. It is also possible to design the expression vector in advance so that the tag may be cleaved and then the peptide may be purified. Furthermore, by the above-described conventional method commonly used in the field of peptide chemistry, the hemagglutinin-binding peptide or influenza virus infection-inhibiting peptide may be purified.

==Chemical Modification of the Hemagglutinin-Binding Peptide and Influenza Virus Infection-Inhibiting Peptide==

Further, the hemagglutinin-binding peptide and influenza virus infection-inhibiting peptide of the invention can be suitably modified. For example, by chemical modification, such as alkylation, lipidation (phospholipidation), or the like, the cell affinity or tissue affinity of the hemagglutinin-binding peptide and influenza virus infection-inhibiting peptide can be enhanced and its half-life in blood can be extended, whereby its pharmacological effect can be enhanced.

Alkylation of the hemagglutinin-binding peptide and influenza virus infection-inhibiting peptide can be performed in accordance with the conventional method. For example, alkylation can be easily performed by an amide bond-forming reaction between a fatty acid and the N-terminal amino group of the hemagglutinin-binding peptide, as with the above-described peptide synthesis. The fatty acid to be used can be widely selected and a straight-chain acid or a branched-chain acid, saturated or unsaturated, may be used, but particularly preferred is a fatty acid present in the living body. Specific examples of such fatty acid include fatty acids of about 12 to 20 carbon atoms: saturated fatty acids such as lauric acid, myristic acid, palmitic acid, stearic acid, arachic acid, etc.; and unsaturated fatty acids such as oleic acid, eraidic acid, rinolic acid, linolenic acid, arachidonic acid, etc.

The alkylation can also be performed by an amide bond-forming reaction between an alkylamine and the C-terminal carboxyl group of the hemagglutinin-binding peptide, as with the above-described peptide synthesis. The alkylamine to be used can be selected from among various alkylamines, as with the above-mentioned fatty acids, but particularly preferred is an alkylamine having fatty acid chains (of about 12 to 20 carbon atoms) present in the living body.

Lipidation of the hemagglutinin-binding peptide and influenza virus infection-inhibiting peptide can also be performed in accordance with the conventional method (for example, refer to New Current, 11 (3), 15-20 (2000); Biochemica et Biophysica Acta., 1128, 44-49 (1992); FEBS Letters, 413, 177-180 (1997); J. Biol. Chem., 257, 286-288 (1982), etc.). For example, a phospholipid can be attached to the 2-hydroxyl group or 3-phosphoric group of the hemagglutinin-binding peptide and influenza virus infection-inhibiting peptide via a spacer by the condensation method. Where necessary, a reactive SH group to be used for the condensation can be introduced in advance by adding a cysteine-containing amino acid sequence, whose length is not particularly limited but is usually several amino acid residues, to the N- or C-terminus of the hemagglutinin-binding peptide or influenza virus infection-inhibiting peptide. The phospholipid used in this lipidization is not particularly limited, and, for example, phosphatidic acid, phosphatidylcholine (lecithin), phosphatidylethanolamine, phosphatidylserine, phosphatidylinositol, phosphatidylglycerol, etc., all of which consists of the above-mentioned fatty acids, can be used.

Such alkylated or lipidized hemagglutinin-binding peptide and influenza virus infection-inhibiting peptide (lipopeptide) according to the present invention can be used as the lipid component when liposomes are prepared. In that case, the hemagglutinin-binding peptide or influenza virus infection-inhibiting peptide is presented on the liposome, and as a result, it can effectively function as a liposome agent as described hereafter.

==Liposome Containing the Hemagglutinin-Binding Peptide or Influenza Virus Infection-Inhibiting Peptide==

The hemagglutinin-binding peptide or influenza virus infection-inhibiting peptide according to the present invention can be prepared as a liposome agent. In this liposome agent, the hemagglutinin-binding peptide or influenza virus infection-inhibiting peptide according to the present invention is retained in liposomes whose membrane consists of only acidic phospholipid(s) or both of neutral and acidic phospholipids.

Examples of the acidic phospholipids to constitute the membrane include natural or synthetic phosphatidylglycerols (PGs) such as dilauroylphosphatidylglycerol (DLPG) dimyristoylphosphatidylglycerol (DMPG) dipalmitoylphosphatidylglycerol (DPPG), distearoylphosphatidylglycerol (DSPG) dioleoylphosphatidylglycerol (DOPG), egg yolk phosphatidylglycerol (egg yolk PG), hydrogenated egg yolk phosphatidylglycerol; and natural or synthetic phosphatidylinositols (PIs) such as phosphatidylinositol dimyristoylphosphatidylinositol dipalmitoylphosphatidylinositol (DPPI), distearoylphosphatidylinositol (DSPI), dioleoylphosphatidylinositol (DOPI), soybean phosphatidylinositol (soybean PI), and hydrogenated soybean phosphatidylinositol. Each of these acidic phospholipids can be used alone or in combination of two or more.

Examples of the neutral phospholipids include natural or synthetic phosphatidylcholines (PCs) such as soybean phosphatidylcholine, egg yolk phosphatidylcholine, hydrogenated soybean phosphatidylcholine, hydrogenated egg yolk phosphatidylcholine, dimyristoylphosphatidylcholine dipalmitoylphosphatidylcholine (DPPC), dilauroylphosphatidylcholine (DLPC), distearoylphosphatidylcholine (DSPC), myristoylpalmitoylphosphatidylcholine (MPPC), palmitoylstearoylphosphatidylcholine (PSPC) and dioleoylphosphatidylcholine (DOPC); and natural or synthetic phosphatidylethanolamines (PEs), such as soybean phosphatidylethanolamine, egg yolk phosphatidylethanolamine, hydrogenated soybean phosphatidylethanolamine, hydrogenated egg yolk phosphatidylethanolamine, dimyristoylphosphatidylethanolamine (DMPE), dipalmitoylphosphatidylethanolamine (DPPE), dilauroylphosphatidylethanolamine (DLPE), distearoylphosphatidylethanolamine (DSPE), myristoylpalmitoylphosphatidylethanolamine (MPPE), palmitoylstearoylphosphatidylethanolamine (PSPE) and dioleoylphosphatidylethanolamine (DOPE). Each of these neutral phospholipids can be used alone or in combination of two or more.

The aforementioned liposome membrane is formed, according to the conventional method by using either the aforementioned acidic phospholipid(s) alone or neutral and acidic phospholipids in combination, as the constituent of the membrane. In this preparation, acidic phospholipid is contained, by proportion, about 0.1 to about 100 mol %, preferably about 1 to about 90 mol %, more preferably about 10 to about 50 mol %, in the liposome membrane constituents.

For example, cholesterol etc. can be added when preparing the above-mentioned liposomes. By adding cholesterol, the fluidity of phospholipid can be adjusted so that liposomes can be prepared more simply and conveniently. Typically, cholesterol can be added at or up to an equal volume to phospholipid, preferably in a 0.5 to 1-fold volume.

In the preparation of the liposome, the ratio of the molecular number between the lipidized hemagglutinin-binding peptide or influenza virus infection-inhibiting peptide and the acidic phospholipid is typically about 1:0.5 to 100, preferably about 1:1 to 60, and more preferably about 1:1.5 to 20.

For example, multilayer vesicles (MLVs) are prepared using the phospholipid, as follows. First, the lipid is dissolved in an organic solvent such as chloroform and ether, and then put in a round bottom flask. The organic solvent is removed under nitrogen current or under reduced pressure to form a thin lipid film at the bottom of the flask. Optionally, the flask may be left in a desiccator under reduced pressure for complete removal of residual solvent. Subsequently, the lipid is hydrated by adding an aqueous solution of the lipidized hemagglutinin-binding peptide to the thin lipid film to yield a turbid, opalescent liposome suspension.

Large unilamellar vesicles (LUVs) can be produced as follows: $Ca^{2+}$ is added to small unilamellar phosphatidylserine vesicles, which are then fused to form a cylindrical sheet, followed by addition of the chelating agent EDTA to remove the $Ca^{2+}$ (Biochim. Biophys. Acta 394, 483-491, 1975). LUVs can also be produced by injecting the lipid in ether into an aqueous solution at about 60° C. and evaporating the ether (Biochim. Biophys. Acta 443, 629-634, 1976).

In addition, peptide-incorporated liposomes can be prepared by adding the aqueous solution of a peptide to the prepared liposome suspension.

Besides these methods, a liposome with small particle-size can be prepared by the French press method (FEBS lett. 99, 210-214, 1979). The freeze-drying method (Chem. Pharm. Bull, 32, 2442-2445, 1984) for a liposome with a high capacity, and the freezing-thawing method (Chem. Pharm. Bull. 33, 2916-2923, 1985), both of which were reported by Ohsawa et al., may also be adopted.

The content of the lipidized hemagglutinin-binding peptide or influenza virus infection-inhibiting peptide contained in a liposome prepared in this manner may be a few to a few tens of mol % of all the lipids, preferably 5 to 20 mol %, but, typically, about 5 mol %.

Further, the liposomes thus prepared can be made homogeneous in terms of particle size by dialysis (J. Pharm. Sci. 71, 806-812, 1982) or by a filtrating method using a polycarbonate membrane (Biochim. Biophys. Acta 557, 9-23, 1979; Biochim. Biophys. Acta 601, 559-571, 1980). To remove the lipidized hemagglutinin-binding peptide or the influenza virus infection-inhibiting peptide from the prepared liposome solution, which has not been retained in the liposome, dialysis, a gel filtration method, or a centrifugation method can be used (see "Liposome. Shishitsu no Kagaku" (Chemistry of lipids); Biochemical Experiment Lecture 3, edited by the Japanese Biochemical Society, published by Tokyo Kagaku Dojin, 1974). Further, the liposome can be also concentrated by using a dialysis membrane.

The liposome dispersion thus prepared may appropriately contain various kinds of known substances, such as antiseptics, isotonizing agents, buffers, stabilizers, solubilizing agents, and absorption accelerators, etc, as required additives for formulating the preparation. The liposome dispersion can also be diluted with a solution containing these additives or with water, if required. Specific examples of the above-mentioned additives include: preservatives, which are effective for fungi and bacteria, such as benzalkonium chloride, benzethonium chloride, chlorhexidine, parabens (methyl paraben, ethyl paraben, etc.), and thimerosals; isotonizing agents, such as D-mannitol, D-sorbitol, D-xylitol, glycerol, glucose, maltose, sucrose, and electrolytes (e.g., polyhydric alcohols and sodium chloride); and stabilizers, such as tocopherol, burylhydroxyanisole, butylhydroxytoluene, ethylenediaminetetraacetic acid salt (EDTA), and cysteine.

Additionally, liposome agents can be manufactured by further encapsulating another agent, for example, an antiviral agent, into the above-mentioned liposome containing the hemagglutinin-binding peptide according to the present invention.

The liposome agent may be manufactured in accordance with the methods specifically described in the reference by, for example, Woodle et al. (Long Circulating Liposomes: old drug, New therapeutic., M. C. Woodle, G. Storm, Eds: Springer-Verlag, Berlin (1998)) or Namba et al. (Liposomal applications to cancer therapy, Y. Namba, N. Oku, J. Bioact. Compat. Polymers, 8, 158-177 (1993)).

The content of the hemagglutinin-binding peptide or influenza virus infection-inhibiting peptide in the liposome agent according to the present invention is not limited and may be appropriately selected; it is typically about 0.0002 to 0.2 (w/v %), preferably about 0.001 to 0.1 (w/v %) in the composition.

==Peptide Aggregate==

The hemagglutinin-binding peptide or influenza virus infection-inhibiting peptide may be used without processing as an influenza virus-infection inhibitor, but by forming peptide aggregates, it can inhibit the infection of an influenza virus to a host cell with higher efficiency. The peptide aggregate as described herein refers to micelle (i.e. sphere with the hydrophobic group facing inward and the hydrophilic group positioned outward), or a self-assembled peptide (i.e. peptide aggregate with a diameter of a few hundreds of nanometers to a few micrometers spontaneously assembled in a solution).

In this method, production of an amphiphilic compound having both the hydrophilic and hydrophobic character by modifying the hemagglutinin-binding peptide or the influenza virus infection-inhibiting peptide can facilitate the formation of a peptide aggregate. For example, an amphiphilic compound can be prepared by alkylating the hemagglutinin-binding peptide or influenza virus infection-inhibiting peptide. Alkylation can be performed as described above.

When the concentration of the hemagglutinin-binding peptide, or the influenza virus infection-inhibiting peptide, or the amphipathically-modified hemagglutinin-binding peptide or the influenza virus infection-inhibiting peptide reaches a critical point in fluid, they aggregate to form peptide aggregates. The peptide aggregates can be thus formed by suspending the hemagglutinin-binding peptide or the influenza virus infection-inhibiting peptide in the predetermined or higher concentration. It is conceived that the formation of the peptide aggregates of the hemagglutinin-binding peptide or the influenza virus infection-inhibiting peptide is also effective in statically inhibiting the binding between hemagglutinin and the influenza virus receptor present on a host cell. The diameter of a peptide aggregate can be measured using, for example, light intensity distribution (intensity PSD).

==Pharmaceutical Composition in Other Forms==

Instead of administering the hemagglutinin-binding peptide or influenza virus infection-inhibiting peptide described so far, an expression vector capable of expressing the peptide may be administered. The vector may be a plasmid or a viral vector, but it should have a promoter capable of expressing the inserted gene in a cell to be used. As for the administration method, DNA may be administered as it is; a virus containing DNA may be infected; and a cell containing DNA may be transplanted. The virus is not particularly limited but illustratively an adenovirus or a retrovirus, etc. may be used. Preferably, the vector is constructed so that the virus is capable of infecting cells in the body, and expressing and secreting the hemagglutinin-binding peptide or the influenza virus infection-inhibiting peptide. Likewise, in the case of cell transplantation, preferably the vector is constructed so that cells are capable of expressing and secreting the hemagglutinin-binding peptide or the influenza virus infection-inhibiting peptide. To make the expressed peptide secreted by the cells, for example, the vector is constructed so that cells express the hemagglutinin-binding peptide or influenza virus infection-inhibiting peptide fused with a signal peptide at the N-terminus. However, the method for secretion is not necessarily limited to this technique.

EXAMPLES

Example 1

First, using the phage display system used in the report of Nishi, Saya, et al. (Nishi T., Saya H., et al., FEBS Lett, 399, 237-240 (1996)), filamentous phages fd which present peptides having the amino acid sequences of SEQ ID NOs: 1 to 18 on the surface of their coat were prepared as follows. By inserting DNAs encoding these amino acid sequences (see the above-mentioned table 1) into the region corresponding to the N-terminal region of the coat protein pIII by genetic recombination techniques, phage DNAs can be constructed such that peptides having 15-residue amino acid sequences encoded by the inserted DNAs are expressed on the surface of the phage coat. Each of these phages were amplified using the K91Kan host bacteria and phage solution was prepared by a conventional method.

Next, the binding of these phages to hemagglutinin (HA), which presented each of the amino acid sequences of SEQ ID NOs: 2 to 18 on their surface was examined by ELISA. To prepare the hemagglutinin (HA) immobilized on the plate, an ether extract of the type A subtype H1 A/PR/8/34 (H1N1) and an ether extract of the type A subtype H3 A/Wuhan/359/95 (H3N2) were used. Specific procedures are described as follows.

First, to activate the carboxyl group bound to 96-well carboplates (SUMILON), 60 μl of a 1:1 mixture of EDC (1-athyl-3-(3-dimethylaminopropyl)carbodiimide) and N-hydroxysuccinimide was added to each well of the plates, and left for 10 min.

Next, to immobilize hemagglutinin on the activated plates, each well was washed 6 times with 50 mM TBS buffer solution (pH 7.6) and 100 μl of solution of H1N1 (70 μl/ml) or solution of H3N2 (70 μl/ml) was added. After the plate was left for 2 h, the wells were washed 6 times with 50 mM TBS buffer solution (pH 7.6), and 100 μl of 1 mM ethanolamine aqueous solution was added. After the plate was left for 10 min, the wells were washed 6 times with 50 mM TBS buffer solution (pH 7.6) again.

50 μl solution (containing $1\times10^{10}$ pfu) of each phage clone was added to the plates in which hemagglutinin was immobilized, followed by incubation at room temperature for 2 h. After each well was washed 5 times with TEST (TBS/5% Tween20), 100 μl of anti-fd phage antibody (manufactured by Sigma Chemical Co.; used at 1000-fold dilution) diluted with 1% BSA-containing TBST was added, followed by incubation at room temperature for 1 hr. After each well was washed 5 times with TBST (TBS/5% Tween20), 100 μl of HRP-conjugated anti-rabbit IgG antibody (manufactured by Sigma Chemical Co.; used at 1000-fold dilution) diluted with 1% BSA-containing TBST was added, and incubated at room temperature for 1 hr. After each well was washed 5 times with TBST (TBS/5% Tween20), 100 μl of peroxidase (POD) solution was added as substrate, followed by incubation for 10 to 15 min. The reaction was terminated by adding 3N $H_2SO_4$, the absorption at 492 nm was measured with a microplate reader to obtain the binding activity.

Figure 2:
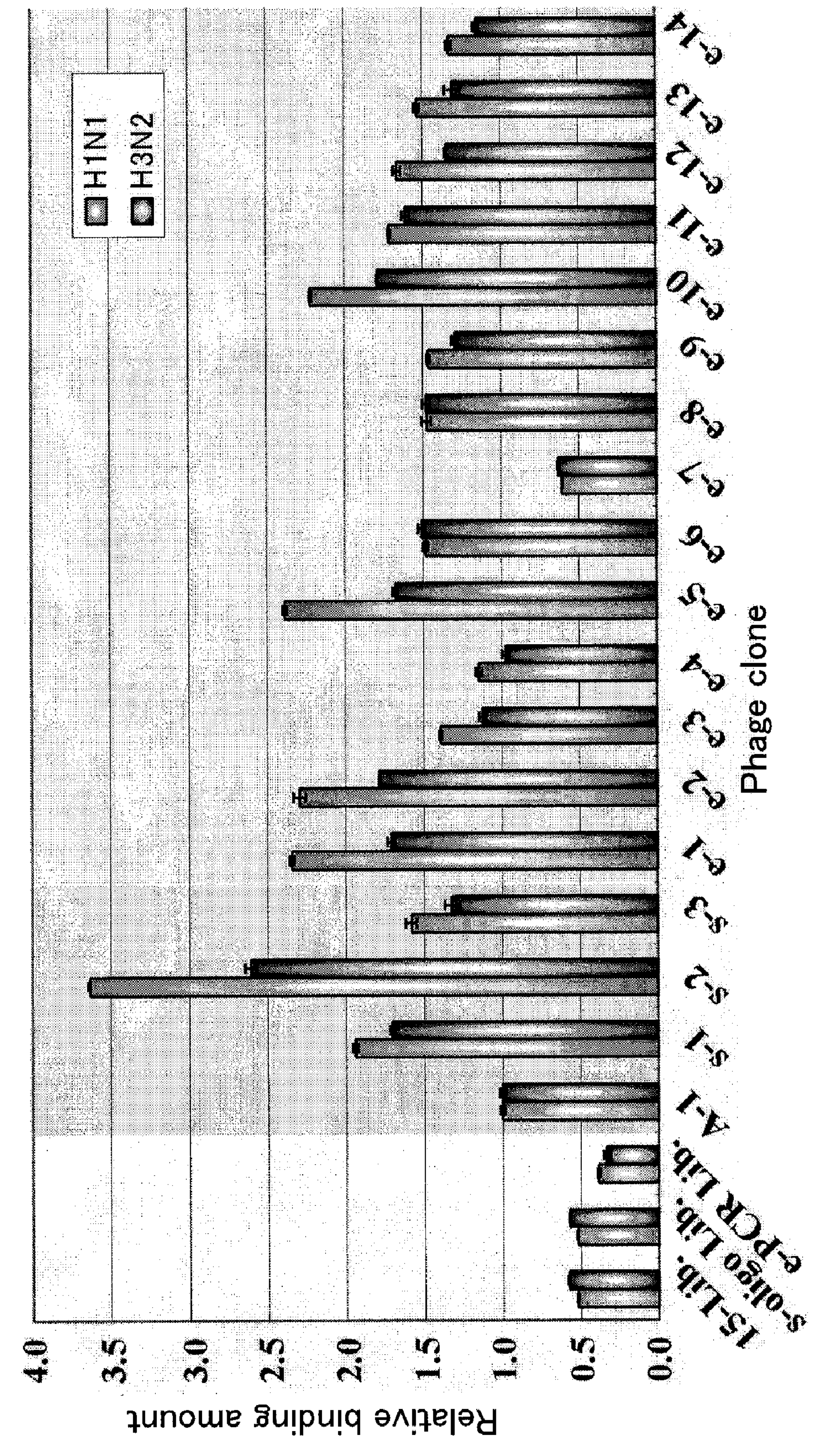
FIG. 2 shows a graph comparing the binding activities of peptides having the amino acid sequence of SEQ ID NOs: 2 to 18 to hemagglutinin with that of A-1 (SEQ ID NO: 1) using ELISA in an example according to the present invention.

This binding activity was compared with the binding activities of the primary phage display library, the secondary phage display library, and A-1 (SEQ ID NO: 1) as controls, which were described above. A-1 has binding activity comparable to that of the hemagglutinin-binding peptides identified so far (WO00/59932 and Japanese Laid-Open Application No. 2002-284798). As an example, the comparison with the binding activity of H3G-1 measured in the same manner is shown in FIG. 1. Here, all the data on the binding activities of peptides having the amino acid sequences of SEQ ID NOs: 2 to 18 were normalized by taking the binding activity of A-1 to each of H1N1 and H3N2 as 1, and plotted on a graph (FIG. 2). This graph in FIG. 2 indicated that the peptides other than e-4 and e-7 had stronger binding activity to both types of hemagglutinin than A-1 did. In particular, s-2 exhibited about 3-fold stronger binding activities than A-1. Each of the aforementioned libraries had merely a several-fold weaker activity than A-1.

Taken together, it is concluded that the polypeptides having SEQ ID NOs: 2 to 7, 9 to 10, and 12 to 18 have higher binding activity to hemagglutinin than the hemagglutinin-binding peptide having the amino acid sequence of SEQ ID NO: 1, and thus useful as a pharmaceutical composition, one of the goals of the present invention.

It should be noted that since these sequences have a common sequence (consensus sequence) of xRL (S/P) xxMV (H/R) xxxxQx (SEQ ID NO: 37), the polypeptides having this common sequence are considered to have higher binding activity to hemagglutinin than the hemagglutinin-binding peptide having the amino acid sequence of SEQ ID NO: 1.

Example 2

The peptides having the sequence of s-2 (SEQ ID NO: 3) and the sequence of e-1 (SEQ ID NO: 5), which showed outstandingly high binding to hemagglutinin in the ELISA in Example 1, were chemosynthesized and their binding to hemagglutinin was evaluated in the form of peptide alone. It should be noted that the synthesis was contracted to Toray Industries, Inc.

The peptides used in this Example and their amino acid sequences are shown in Table 3.

TABLE 3

| Name | a. a. seq. | MW | |
|---|---|---|---|
| A-1 | ARLSPTMVHPNGAQP-$NH_2$ | 1575 | (SEQ ID: 1) |
| s-2 | ARL**PR**TMVHP**KP**AQP-$NH_2$ | 1698 | (SEQ ID: 3) |
| e-1 | ARL**P**PTMV**R**PNG**P**QP-$NH_2$ | 1630 | (SEQ ID: 5) |
| pVIII | AEGDDPAKAAFDSLQ-$NH_2$ | 1534 | (SEQ ID: 51) |

By using these hemagglutinin-binding peptides, their binding to the hemagglutinin-immobilized membrane was evaluated as follows. H3N2 was immobilized on Sensor ChipCM5 (Biacore, BR-1000-14), as with the plate used in Example 1. The binding activity of the peptides to this immobilized H3N2 was evaluated using the Biacore system (Biacore). Specifically, time-course changes of the resonance was measured for each of the peptides at various concentrations.

Figure 3A:
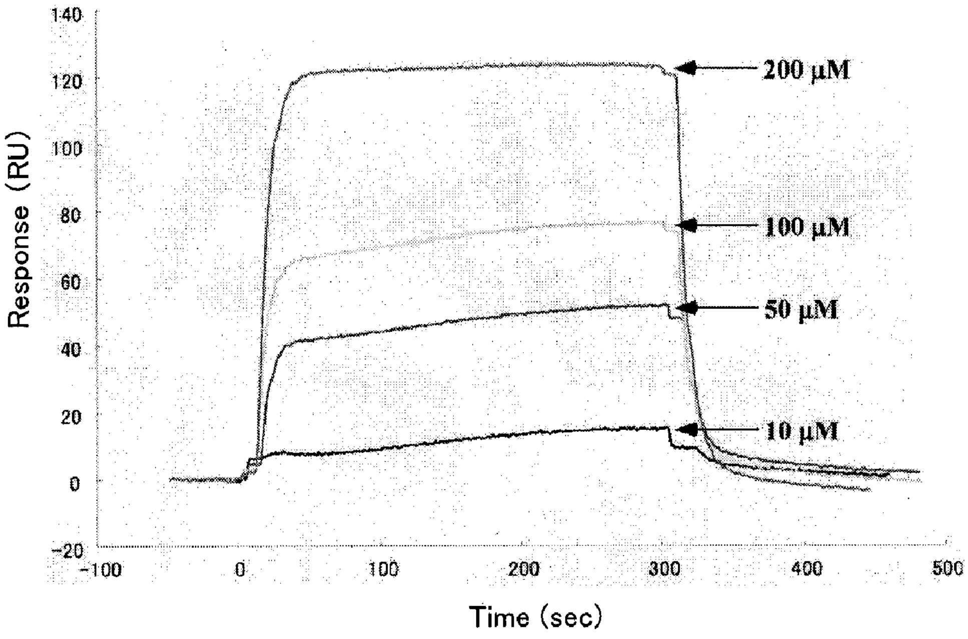
FIG. 3 (A) is a figure showing the relationship between time (x-axis) and the resonance (y-axis) of s-2 peptide at each of several concentrations in an example according to the present invention. (B) is a graph showing the changes of the resonance (y-axis) relative to the concentration (x-axis) of each of the hemagglutinin-binding peptides at a predetermined time in an example according to the present invention.
Figure 3B:
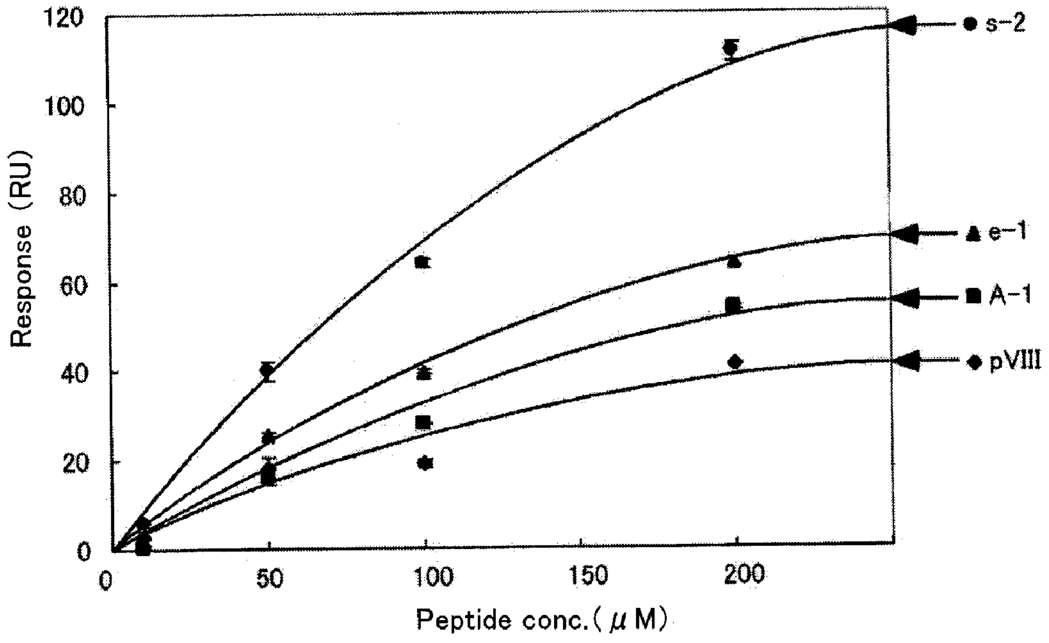

First, the relationship between time (x-axis) and resonance (y-axis) at each concentration of s-2 peptide is shown in FIG. 3A. Then, similar experiments were conducted with each of hemagglutinin-binding peptides, and changes of the resonance (y-axis) relative to the concentration (x-axis) in predetermined time were plotted as shown in FIG. 3B. As shown in the figures, it was found that the amounts of binding to hemagglutinin of each hemagglutinin-binding peptide increased depending on the concentrations.

Figure 4A:
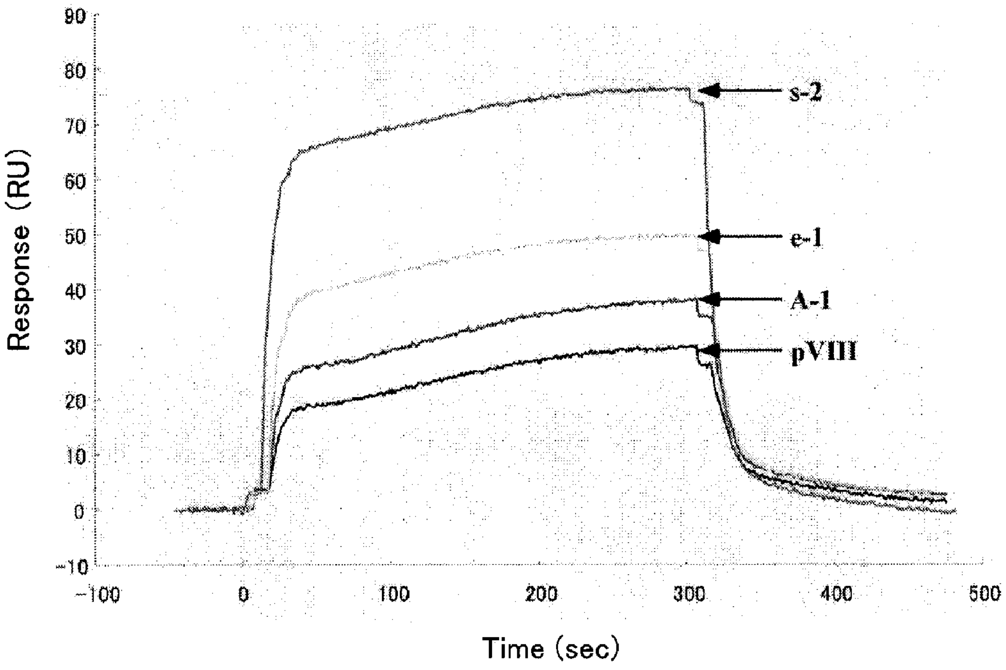
FIG. 4 (A) shows a graph indicating the changes of the resonance (y-axis) relative to time (x-axis) at 100 μM of each hemagglutinin-binding peptide. (B) shows the relative values of the hemagglutinin-binding peptides when the amount of binding of A-1 peptide was taken as 1 at 200 μM of each hemagglutinin-binding peptide in an example according to the present invention.
Figure 4B:
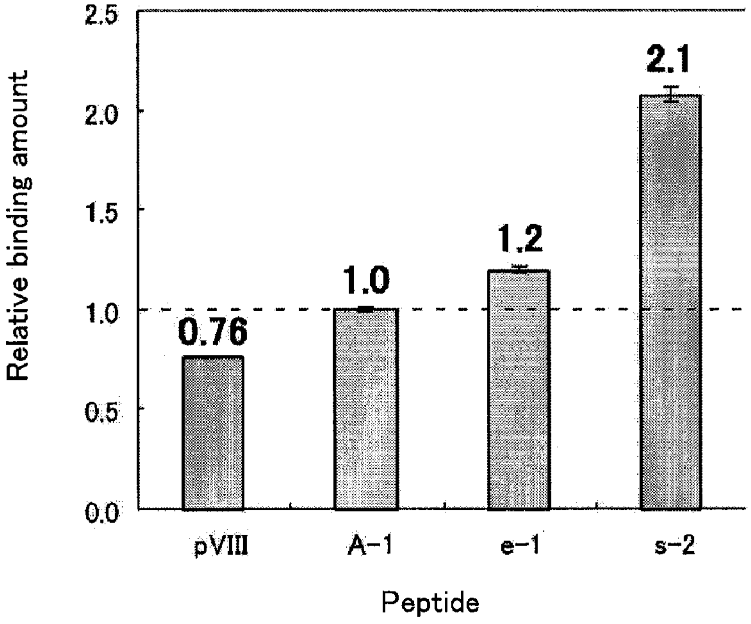

Next, based on these results, the bindings of the hemagglutinin-binding peptides were compared at the predetermined peptide concentrations. FIG. 4A shows changes in resonance (y-axis) relative to the time (x-axis) course at a peptide concentration of 100 μM of each hemagglutinin-binding peptide. FIG. 4B shows the relative value of the resonance of each hemagglutinin-binding peptide when the amount of binding of A-1 peptide was taken as 1 at a peptide concentration of 200 μM. As shown in the figures, it was found that the peptides were bound to hemagglutinin in the order of binding strength, s-2>e-1>A-1>pVIII (SEQ ID NO: 51). This order of binding strength was also consistent with the order of binding strength measured using the phages expressing each of the hemagglutinin-binding peptides.

The results revealed that e-1 and s-2 were bound to hemagglutinin 1.2-fold and 2.1-fold more strongly than A-1 did, respectively, suggesting that substitutions of amino acids improved the function of the peptides. Although the amount of bindings to hemagglutinin was too small to obtain the dissociation constant $K_d$, the theoretical maximum amount of binding was calculated to be 228 RU based on the amount of the ligands immobilized in this experiment. Since the amount of binding of, for example, s-2 at 200 μl is approximately half of 228 RU, the dissociation constants of these peptides are inferred to be about $10^{-3}$ to $10^{-4}$M.

Inhibition of the interaction between GM3 and hemagglutinin (HA) was evaluated by ELISA using the GM3 cast membrane (Kazuhiro Nagata and Hiroshi Handa, "Seibutsu Busshitsu Sogosayo no Real-time Kaiseki Jikkenho—BIACORE wo Chushin Ni (Real-time Analysis Experimental Procedures on Biological Substance Interaction—Focusing on BIOCORE), Springer-Verlag Inc., Tokyo, 1998)"). As a result, peptide A-1 inhibited the binding of hemagglutinin to GM3 in the order of mM ($IC_{50}$ of A-1 to H3=1.9 mM). In addition, it has been reported from an evaluation by NMR that the binding constant between hemagglutinin and free sialyl lactose is in the order of mM (e.g. α (2, 3)-sialyllactose $K_0$=3.2 mM). Therefore, the results presented in this Example were largely consistent with the inhibition constant of the peptides reported by Inoue. Moreover, the results presented in this Example are in the same order of magnitude as, or one order smaller than, the inhibition constant of A-1 or the binding constant obtained with sialyl lactose. It was therefore suggested that these hemagglutinin-binding peptides could serve as excellent analogs of sugar chains, the ligands for hemagglutinin.

Example 3

While Example 1 revealed that the polypeptides having SEQ ID NOs: 2 to 7, 9 to 10, and 12 to 18 had high binding activity to hemagglutinin, identification of peptides having even fewer residues capable of preventing influenza virus infection was attempted in the following experiments.

(1) Preparation of Alkylated Peptides

In order to form peptide aggregates, alkylated peptides were used in this experiment.

First, the peptides shown in the following table 4 (SEQ ID NOs: 1, 3, 38 to 47, and 52 to 55) were synthesized using the automatic peptide synthesizer PSSM-8 (Shimadzu Co.) by employing Fmoc method. Synthesis reaction of the peptides was performed using Fmoc-SAL-Resin (code A00102, Watanabe Chemical Industries, Ltd.) as solid phase resin. Next, C18-COOH (stearic acid, Sigma) dissolved in dichloromethane was reacted on the solid phase resin after the peptide synthesis to alkylate the N-terminus of these peptides. Then, C18 peptide was excised from the synthesized solid-phase resin to yield C18 peptide amide (with —$CONH_2$ as its C-terminus).

After partial purification, C18 peptide amide was purified by high performance liquid chromatography (HPLC). Further, the molecular weight of the peptide after purification was measured by matrix assisted laser desorption/ionization time-of-flight mass spectrometry (MALDI-TOF MS). For MS measurement, Autoflex™ (Bruker Daltonics) was employed using a matrix of α-cyano-4-hydroxy-cinnamic acis (α-CHCA).

(2) Evaluation of Inhibitory Activity Against Influenza Virus Infection Using a Plaque Assay The following experiment was conducted in order to examine to what extent the various peptides prepared in (1) would inhibit influenza virus infection into host cells.

First, using Minimum Essential Eagles' Medium (MEM; GIBCO BRL), supplemented with 10% fetal bovine serum, 0.1% $NaHCO_3$, 10 μg/ml glutamine, 100 units/ml penicillin G, and 100 units/ml streptomycin, Mardin-Darby canine kidney (MDCK) cells were cultured in 6-well microplates as a monolayer in a 5% $CO_2$ incubator at 37° C. until confluence was reached. The MDCK cells as well as the influenza virus A/Puerto Rico/8/34 strain (H1N1) and the influenza virus A/Aichi/2/68 strain (H3N2) used in the following experiments were provided by K. Nagata (University of Tsukuba, Japan). It should be noted that MDCK cells are widely used in influenza virus infection experiments because they exhibit high sensitivity to all of influenza viruses type A, type B, and type C, and hemagglutinin mutants do not appear during cell growth.

Next, 100 μL of H1N1 influenza virus solution (a solution of type A influenza virus/PR/8/34 diluted to the concentration to form around 100 plaques) or H3N2 influenza virus solution (a solution of type A influenza virus/Aichi/2/68 diluted to the concentration to form around 100 plaques) was mixed with 100 μL of various peptide solutions (peptide concentrations 0.2 to 200 μM) to prepare totally 200 μL of samples.

Next, the media in the 6-well microplates was removed and the surface of cells were washed with 1 to 2 mL of PBS(−) per each well. After removal of the PBS (−), the samples prepared as described above were transferred to the plates (200 μL/well), which were then incubated at 37° C. in a 5% $CO_2$ incubator.

After 30 min, the solutions in the samples were removed and the surface of the cells was washed with 1 to 2 mL of PBS (−) per each well. Next, 0.625 ml/well of 2% agar (Oxoid, LTD., product number: L28) preheated at 50° C. was mixed with 1.475 ml/well of overlay medium and dispensed at 2 mL/well. It should be noted that the overlay medium was made, for a volume of 6 wells, by mixing 6.25 ml of 2×MEM+BA, 2.25 ml of purified water, 0.125 ml of 1% DEAE dextran, 0.167 ml of 7.5% $NaHCO_3$, and 0.125 ml of acetyltrypsin (1 mg/ml PBS) and that 2×MEM+BA was prepared from 9.4 g of MEM added to 474 mL of MiliQ water, which was autoclaved and then added with 10 mL of L-glutamine solution sterilized by filtration (×100, 30 mg/mL), 10 mL of 1M Hepes (2.4 g/10 mL), and 6 mL of 35% bovine albumin (A-7409, Sigma). The plates were then incubated at room temperature for 30 min. The agar was reversed when solidified, and then incubated at 37° C. in 2.5% $CO_2$ incubator for 2 days.

Two days after the infection of the influenza virus, the overlay medium was removed and the plate was dried. Next, after staining was performed for 5 min by adding 500 μL/well of crystal violet staining solution (50 mg Crystal Violet/50 mL 20% ethanol), the wells were washed with purified water 5 times and air-dried. Finally, the number of plaques was counted and the resulting values were compared with those obtained from the control (i.e. samples which were incubated with the influenza virus only) to determine the inhibition rate of influenza virus infection using each peptide.

The result of infection rates of the H1N1 or H3N2 influenza virus using various peptides is shown in FIG. 4. C18-s2 (r1-8) was used as the negative control. C18-s2 (r1-8) (SEQ ID NO: 41) is a peptide having the same amino acid composition as s2 (1-8) (SEQ ID NO: 38) with a different sequence. $IC_{50}$ refers to the peptide concentration required to inhibit the infection by 50% when the infection rate without peptides was taken as 100%.

TABLE 4

| Category | Peptide | Peptide seq. | Seq. No. | Residues | $IC_{50}$ (μM) H1 | H3 |
|---|---|---|---|---|---|---|
| #1 | C18-A1 | C18-ARLSPTMVHPNGAQP | 1 | 15 | 195 | 365 |
| | C18-s2 | C18-ARLPRTMVHPKPAQP | 3 | 15 | 10 | 8.2 |
| #2 | C18-s2(1-8) | C18-ARLPRTMV | 38 | 8 | 2.4 | 1.4 |
| | C18-s2(5-11) | C18-RTMVHPK | 39 | 7 | 11 | >100 |
| | C18-s2(8-15) | C18-VHPKPAQP | 40 | 8 | 59 | 10.5 |
| | C18-s2(r1-8) | C18-VMTRPLRA | 41 | 8 | 93 | 226 |
| #3 | C18-s2(1-7) | C18-ARLPRTM | 42 | 7 | 7.1 | 9.1 |
| | C18-s2(1-6) | C18-ARLPRT | 43 | 6 | 3.5 | 5.0 |
| | C18-s2(1-5) | C18-ARLPR | 44 | 5 | 3.1 | 3.0 |
| | C18-s2(1-4) | C18-ARLP | 52 | 4 | 0.9 | 21 |
| | C18-s2(1-4)P4A | C18-ARLA | 53 | 4 | >100 | >100 |
| | C18-s2(1-3) | C18-ARL | 54 | 3 | >100 | >100 |
| | C18-s2(1-2) | C18-AR | 55 | 2 | >100 | >100 |
| #4 | C18-s2(2-8) | C18-RLPRTMV | 45 | 7 | 9.2 | >100 |
| | C18-s2(3-8) | C18-LPRTMV | 46 | 6 | >100 | — |
| | C18-s2(4-8) | C18-PRTMV | 47 | 5 | >100 | — |

As a result, C18-s2 (1-8) peptide (SEQ ID NO: 38), C18-s2 (1-7) peptide (SEQ ID NO: 42), C18-s2 (1-6) peptide (SEQ ID NO: 43), and C18-s2 (1-5) peptide (SEQ ID NO: 44), and C18-s2 (1-4) peptide (SEQ ID NO: 52), all of which were peptides truncated in the C-terminus region of SEQ ID NO: 3 and had the ARLPR (SEQ ID NO: 44) sequence, were capable of inhibiting H1N1 influenza virus infection more strongly than C18-S2 peptide (SEQ ID NO: 3) and inhibiting H3N2 influenza virus infection as strongly as, or more strongly than, C18-S2 peptide (SEQ ID NO: 3).

Further, it was shown that C18-S2 (2-8) peptide was capable of inhibiting H1N1 influenza virus infection as strongly as, or more strongly than, C18-S2 peptide (SEQ ID NO: 3).

In contrast, it was shown that C18-s2 (1-3) peptide (SEQ ID NO: 54) and C18-s2 (1-2) peptide (SEQ ID NO: 55) were unable to inhibit infection of H1N1 and H3N2 influenza viruses.

The above findings revealed that the peptides truncated in the C-terminus region of SEQ ID NO: 3 and having the ARLPR (SEQ ID NO: 44) sequence strongly inhibited influenza virus infection to MDCK cells. It was further revealed that the peptides having the RLPR (SEQ ID NO: 61) sequence that was made by truncating the N-terminus residue strongly inhibited infection of H1N1 influenza virus to MDCK cells. Furthermore, it was revealed that the peptides having the ARLP (SEQ ID NO: 52) sequence truncated in the C-terminus region of SEQ ID NO: 3 also strongly inhibited influenza virus infection into MDCK cells.

In addition, by using the same method as above, a peptide (C18-s2 (r1-5) peptide: SEQ ID NO: 56) having an inverted sequence of the ARLPR sequence (C18-s2 (1-5) peptide: SEQ ID NO: 44) that is truncated in the C-terminus region of SEQ ID NO: 3 and a peptide (C18-s2 (r1-4) peptide: SEQ ID NO: 57) having an inverted sequence of the ARLP sequence (C18-s2 (1-4) peptide: SEQ ID NO: 52) that is truncated in the C-terminus region of SEQ ID NO: 3 were prepared. A result of H1N1 or H3N2 influenza virus infection rate obtained using these peptides by the above-described method is shown in Table 5.

TABLE 5

| Category | Peptide | Peptide seq. | Seq. No. | Residues | $IC_{50}$ (μM) H1 | H3 |
|---|---|---|---|---|---|---|
| #5 | C18-s2(1-8) | C18-ARLPRTMV | 38 | 8 | 2.4 | 1.4 |
| | C18-s2(r1-8) | C18-VMTRPLRA | 41 | 8 | 93 | 226 |
| #6 | C18-s2(1-5) | C18ARLPR | 44 | 5 | 0.35 | 1.55 |
| | C18-s2(r1-5) | C18-RPLRA | 56 | 5 | 0.55 | 0.94 |
| #7 | C18-s2(1-4) | C18-ARLP | 52 | 4 | 0.9 | 21 |
| | C18-s2(r1-4) | C18-PLRA | 57 | 4 | 0.41 | 14 |

The result revealed that C18-s2 (r1-5) peptide (SEQ ID NO: 56) and C18-s2 (r1-4) peptide (SEQ ID NO: 57) were capable of inhibiting infection of H1N1 influenza virus and H3N2 influenza virus to MDCK cells more strongly than C18-s2 (r1-8) (SEQ ID NO: 41).

The present invention has made it possible to provide peptides having 4 to 8 residues capable of inhibiting influenza virus infection to a host. The 4- to 8-residue peptide thus obtained can be synthesized at a lower cost than a 15-residue peptide.

INDUSTRIAL APPLICABILITY

In accordance with the present invention, peptides having a high affinity for hemagglutinin and peptides having a high inhibitory activity against influenza virus infection can be provided, and further pharmaceutical compositions using such a peptide having high affinity for hemagglutinin or a peptide having high inhibitory activity against influenza virus infection can be provided.

The invention claimed is:

1. A method for inhibiting influenza virus infection in a cell or an animal, comprising administering a peptide to the cell or the animal, the peptide having 4 to 14 amino acid residues and comprising the amino acid sequence of $X_1X_2X_3X_4$(SEQ ID NO: 58), wherein
$X_1$ is alanine, glycine, isoleucine, valine, or leucine;
$X_2$ is arginine or lysine;
$X_3$ is alanine, glycine, isoleucine, valine, or leucine; and
$X_4$ is proline.

2. A method for treating influenza virus infection in an animal, comprising administering a peptide to the animal, the peptide having 4 to 14 amino acid residues and comprising the amino acid sequence of $X_1X_2X_3X_4$(SEQ ID NO: 58), wherein
$X_1$ is alanine, glycine, isoleucine, valine, or leucine;
$X_2$ is arginine or lysine;
$X_3$ is alanine, glycine, isoleucine, valine, or leucine; and
$X_4$ is proline.

3. The method of claim 1, wherein the peptide is modified so as to have amphiphilicity and form a peptide aggregate, wherein said modified peptide has 4 to 14 amino acids residues and comprises the amino acid sequence of $X_1X_2X_3X_4$(SEQ ID NO: 58), wherein
$X_1$ is alanine, glycine, isoleucine, valine, or leucine;
$X_2$ is arginine or lysine;
$X_3$ is alanine, glycine, isoleucine, valine, or leucine; and
$X_4$ is proline.

4. The method of claim 3, wherein the modification is alkylation of an N-terminal amino group of said peptide.

5. The method of claim 1, wherein the peptide has a part of the amino acid sequence of ARLPRTMVHPKPAQP (SEQ ID NO: 3), wherein said peptide has 4 to 14 amino acid residues and comprises the amino acid sequence of $X_1X_2X_3X_4$(SEQ ID NO: 58), wherein
$X_1$ is alanine, glycine, isoleucine, valine, or leucine;
$X_2$ is arginine or lysine;
$X_3$ is alanine, glycine, isoleucine, valine, or leucine; and
$X_4$ is proline.

6. The method of claim 1, wherein the peptide has the amino acid sequence of ARLP (SEQ ID NO: 52).

7. The method of claim 1, wherein the peptide has the amino acid sequence of $X_1X_2X_3X_4X_5$ (SEQ ID NO: 48), wherein
$X_5$ is arginine or lysine.

8. The method of claim 7, wherein the peptide has a part of the sequence of $X_1X_2X_3X_4X_5X_6X_7X_8HX_9X_{10}X_{11}X_{12}X_{13}X_{14}$ (SEQ ID NO: 50) wherein $X_6$ is serine or threonine;
$X_7$ is cysteine or methionine;
$X_8$ is alanine, glycine, isoleucine, valine, or leucine;
$X_9$ is proline, alanine, or glycine;
$X_{10}$ is arginine or lysine;
$X_{11}$ is proline, alanine, or glycine;
$X_{12}$ is alanine, glycine, isoleucine, valine, or leucine;
$X_{13}$ is glutamine or asparagine; and
$X_{14}$ is proline, alanine, or glycine; and wherein said peptide has 4 to 14 amino acid residues and comprises the amino acid sequence of
$X_1X_2X_3X_4$(SEQ ID NO: 58), wherein
$X_1$ is alanine, glycine, isoleucine, valine, or leucine;
$X_2$ is arginine or lysine;
$X_3$ is alanine, glycine, isoleucine, valine, or leucine; and
$X_4$ is proline.

9. The method of claim 8, wherein each of $X_9$, $X_{11}$, and $X_{14}$ is proline.

10. The method of claim 9, wherein the peptide has the amino acid sequence selected from a group consisting of ARLPRTMV (SEQ ID NO: 38), ARLPRTM (SEQ ID NO: 42), ARLPRT (SEQ ID NO: 43), and ARLPR (SEQ ID NO: 44).

* * * * *